United States Patent
Jones et al.

(10) Patent No.: US 10,647,678 B2
(45) Date of Patent: *May 12, 2020

(54) QUINOLINE DERIVATIVES AS INHIBITORS OF HEAT SHOCK FACTOR 1 PATHWAY ACTIVITY

(71) Applicant: Cancer Research Technology Limited, London (GB)

(72) Inventors: Keith Jones, Sutton Coldfield (GB); Matthew Cheeseman, Sutton Coldfield (GB); Nicola Chessum, Sutton Coldfield (GB); Elisa Pasqua, Sutton Coldfield (GB); Lindsay Evans, London (GB); Michael Tucker, Luton (GB); Birgit Wilding, Sutton Coldfield (GB); Ngai Yi Mok, Sutton Coldfield (GB)

(73) Assignee: Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/563,501

(22) PCT Filed: Apr. 1, 2016

(86) PCT No.: PCT/GB2016/050938
§ 371 (c)(1),
(2) Date: Sep. 29, 2017

(87) PCT Pub. No.: WO2016/156872
PCT Pub. Date: Oct. 6, 2016

(65) Prior Publication Data
US 2018/0093955 A1 Apr. 5, 2018

(30) Foreign Application Priority Data

Apr. 1, 2015 (GB) .................... 1505658.3

(51) Int. Cl.
*C07D 215/48* (2006.01)
*C07D 405/12* (2006.01)

(52) U.S. Cl.
CPC ......... *C07D 215/48* (2013.01); *C07D 405/12* (2013.01)

(58) Field of Classification Search
CPC .................................................. C07D 215/48
USPC ....................................................... 546/300
See application file for complete search history.

(56) References Cited

U.S. PATENT DOCUMENTS

| | | | |
|---|---|---|---|
| 5,137,805 A | 8/1992 | Kingston et al. | |
| 5,714,502 A | 2/1998 | Prucher et al. | |
| 5,756,343 A | 5/1998 | Wu et al. | |
| 6,455,520 B1* | 9/2002 | Brown | C07D 213/81 514/217.11 |
| 6,867,036 B1 | 3/2005 | Vile et al. | |
| 8,466,180 B2* | 6/2013 | Jung | C07C 233/80 514/357 |
| 9,701,664 B2* | 7/2017 | Jones | C07D 405/14 |
| 10,189,821 B2* | 1/2019 | Jones | C07D 405/14 |
| 2002/0001629 A1 | 1/2002 | Voellmy | |
| 2002/0058679 A1 | 5/2002 | Yokota et al. | |
| 2005/0192219 A1 | 9/2005 | Voellmy | |
| 2005/0207972 A1 | 9/2005 | Friebe et al. | |
| 2006/0154278 A1 | 7/2006 | Brody et al. | |
| 2007/0105794 A1 | 5/2007 | Lipinski et al. | |
| 2007/0238682 A1 | 10/2007 | Nudler et al. | |
| 2009/0062222 A1 | 3/2009 | Sherman et al. | |
| 2009/0092600 A1 | 4/2009 | Kufe | |
| 2009/0117589 A1 | 5/2009 | Southern | |
| 2009/0163545 A1 | 6/2009 | Goldfarb | |
| 2010/0015605 A1 | 1/2010 | Zucman-Rossi et al. | |
| 2010/0216660 A1 | 8/2010 | Nikolsky et al. | |
| 2011/0112073 A1 | 5/2011 | Thiele et al. | |
| 2011/0123512 A1 | 5/2011 | Prahlad et al. | |

(Continued)

FOREIGN PATENT DOCUMENTS

| | | |
|---|---|---|
| EP | 0995745 A1 | 4/2000 |
| WO | WO-9601825 A1 | 1/1996 |

(Continued)

OTHER PUBLICATIONS

Kim, Bioorganic & Medicinal Chemistry Letters (2012), 22(9), 3269-3273.*

(Continued)

*Primary Examiner* — Nizal S Chandrakumar
(74) *Attorney, Agent, or Firm* — Foley Hoag LLP; David P. Halstead; Lucas P. Watkins

(57) ABSTRACT

The present invention relates to compounds of formula I

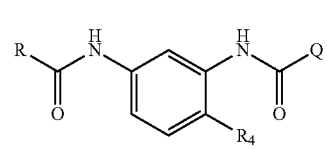

wherein R, $R_4$ and Q are each as defined herein. The compounds of the present invention are inhibitors of heat shock factor 1 pathway (HSF1 pathway). In particular, the present invention relates to the use of these compounds as therapeutic agents for the treatment and/or prevention of proliferative diseases, such as cancer. The present invention also relates to processes for the preparation of these compounds, and to pharmaceutical compositions comprising them.

18 Claims, No Drawings

(56) References Cited

U.S. PATENT DOCUMENTS

| | | |
|---|---|---|
| 2011/0166038 A1 | 7/2011 | Zhang et al. |
| 2011/0166058 A1 | 7/2011 | Hinkle et al. |
| 2011/0182881 A1 | 7/2011 | Chin et al. |
| 2011/0251096 A1 | 10/2011 | Southern |
| 2011/0311508 A1 | 12/2011 | Morimoto et al. |
| 2013/0133108 A1 | 5/2013 | Warpeha et al. |
| 2014/0234858 A1 | 8/2014 | Santagata et al. |
| 2014/0302042 A1 | 10/2014 | Chin et al. |
| 2014/0315214 A1 | 10/2014 | Taipale et al. |
| 2017/0037036 A1 | 2/2017 | Jones et al. |

FOREIGN PATENT DOCUMENTS

| | | | |
|---|---|---|---|
| WO | WO-1998017648 A1 | 4/1998 | |
| WO | WO-9932433 A1 | 7/1999 | |
| WO | WO-99/59959 A1 | 11/1999 | |
| WO | WO-2000007991 A1 | 2/2000 | |
| WO | WO-2000018738 A1 | 4/2000 | |
| WO | WO-0056341 A1 | 9/2000 | |
| WO | WO-2000055153 A1 | 9/2000 | |
| WO | WO-2002036576 A1 | 5/2002 | |
| WO | WO-2003020227 A1 | 3/2003 | |
| WO | WO-2004004703 A1 | 1/2004 | |
| WO | WO-2004006858 A2 | 1/2004 | |
| WO | WO-2004013117 A1 | 2/2004 | |
| WO | WO-2004018414 A2 | 3/2004 | |
| WO | WO-2004019873 A2 | 3/2004 | |
| WO | WO-2004021988 A2 | 3/2004 | |
| WO | WO-2004024083 A2 | 3/2004 | |
| WO | WO-2004056774 A2 | 7/2004 | |
| WO | WO-2005007151 A1 | 1/2005 | |
| WO | WO-2005026334 A2 | 3/2005 | |
| WO | WO-2005042496 A1 | 5/2005 | |
| WO | WO-2006003378 A1 | 1/2006 | |
| WO | WO-2006040568 A1 | 4/2006 | |
| WO | WO-2006124874 A2 | 11/2006 | |
| WO | WO-2007059157 A1 | 5/2007 | |
| WO | WO-2008031534 A1 | 3/2008 | |
| WO | WO-2008077165 A1 | 7/2008 | |
| WO | WO-2008152013 A1 | 12/2008 | |
| WO | WO-2009075874 A1 | 6/2009 | |
| WO | WO-2010043631 A1 | 4/2010 | |
| WO | WO-10053655 A2 | 5/2010 | |
| WO | WO-2010093419 A1 | 8/2010 | |
| WO | WO-11025167 A2 | 3/2011 | |
| WO | WO-13030778 A2 | 3/2013 | |
| WO | WO-13166427 A1 | 11/2013 | |
| WO | WO-13172640 A1 | 11/2013 | |
| WO | WO-14187959 A2 | 11/2014 | |
| WO | WO-2015/049535 A1 | 4/2015 | |
| WO | WO-2016/156872 A1 | 10/2016 | |

OTHER PUBLICATIONS

Zhou, Bioorganic & Medicinal Chemistry Letters (2009), 19(23), 6502-6506.*

Dorwald F. A. Side Reactions in Organic Synthesis, 2005, Wiley: VCH, Weinheim p. IX of Preface p. 1-15.*

Venkatesh, J. Pharm. Sci. 89, 145-54 (2000).*

AKos Screening Library (Aug. 20, 2013) Order No. AKOS006882384 and CHEMCATS accession No. 0097075038 (CAS Registry No. 1298093-46-5).

Ambinter Stock Screening Collection, published Sep. 15, 2014, Order No. Cat. Amb10715307.

Ambinter Stock Screening Collection, published Sep. 15, 2014, Order No. Cat. Amb8261001.

Ashton et al., "New Low-Density Lipoprotein Receptor Upregulators Acting via a Novel Mechanism," J Med Chem, 39(17): 3343-3356 (1996).

Database PubChem Compound [Online] NCBI; Feb. 20, 2008 (Feb. 20, 2008). XP002731865. Database accession No. CID 23854223 abstract.

Hee Jin Kim et al: "New diarylureas and diarylamides possessing acet(benz)amidophenyl scaffold: Design, synthesis, and antiproliferative activity against melanoma cell line", Bioorganic & Medicinal Chemistry Letters, Pergamon, Amsterdam, NL, vol. 22, No. 9, Mar. 6, 2012 (Mar. 6, 2012). pp. 3269-3273, XP028410898, ISSN: 0960-894X, DOI: 10.1016/J.BMCL.2012.03.020 [retrieved on Mar. 11, 2012].

International Search Report and Written Opinion for International Application No. PCT/GB2016/050938 dated May 18, 2016.

Lee et al., "Synthesis of aminoquinazoline derivatives and their antiproliferative activities against melanoma cell line," Bioorgan Med Chem Lee, 20(19): 5722-5725 (2010).

Neustadt et al., "Combinatorial Libraries Based on a Novel and Readily Accessible "Centroid" Scaffold," Tetrahedron Lett, 39(30): 5317-5320 (1998).

Niume et al., "Heat-Resistant Polymers with Thianthrene Analog Units. II. Aromatic Polyamides," J Polym Sci, 18(7): 2163-2174 (1980).

Notice of Allowance and Fees Due for U.S. Appl. No. 15/026,911 dated Apr. 27, 2017.

TimTec Stock Building Blocks and Screening Compounds, published May 16, 2014, Order No. Cat. ST50925835.

Zhou et al., "Synthesis and SAR of novel, non-MPEP chemotype mGluR5 NAMs identified by functional HTS," Bioorgan Med Chem Lett, 19(23): 6502-6506 (2009).

* cited by examiner

QUINOLINE DERIVATIVES AS INHIBITORS OF HEAT SHOCK FACTOR 1 PATHWAY ACTIVITY

This application is the U.S. National Stage of International Patent Application No. PCT/GB16/050938, filed Apr. 1, 2016, which claims the benefit of and priority to Great Britain Patent Application No. 1505658.3, filed Apr. 1, 2015.

INTRODUCTION

The present invention relates to novel compounds that act as inhibitors of heat shock factor 1 (HSF1) pathway activity. The present invention further relates to processes for preparing the compounds defined herein, to pharmaceutical compositions comprising them, and to their use in the treatment of HSF1 pathway mediated conditions or diseases (such as cancer, autoimmune diseases and viral diseases).

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the identification of a number of molecular targets associated with key metabolic pathways that are known to be associated with malignancy.

Heat shock factor 1 pathway (HSF1 pathway) is one target pathway that is of interest. HSF1 is the master regulator of the heat shock response, in which multiple genes are induced in response to temperature increase and other stresses. At non-shock temperatures in humans and other vertebrates, HSF1 is produced constitutively, but is inactive and bound by protein HSP90. At an elevated temperature, HSF1 is released by HSP90, moves from the cytoplasm to the nucleus, and trimerizes. This active HSF1 form binds to sequences called heat shock elements (HSE) in DNA and activates transcription of heat shock genes by RNA polymerase II. The HSE has a consensus sequence of three repeats of NGAAN and is present in the promoter regions of the HSP90, HSP70 and HSP27 genes. During cessation of the heat shock response, HSF1 is phosphorylated by mitogen-activated protein kinases (MAPKs) and glycogen synthase kinase 3 (GSK3) and returns to an inactive state. The biochemistry of HSF1 is described in more detail in, inter alia, Chu et al. 1996 J. Biol. Chem. 271:30847-30857 and Huang et al. 1997 J. Biol. Chem. 272:26009-26016.

HSF1 also interacts with additional factors. For example, HSF1 binds to DNA-dependent protein kinase (DNA-PK), which is involved in DNA repair. HSF1 is also target of mitogen-activated protein kinases, and its activity is down-regulated when the RAS signalling cascade is active.

Additional heat shock factor proteins in humans include HSF2, HSF3, and HSF4. HSF 1, HSF2, and HSF3 are all positive regulators of heat shock gene expression, while HSF4 is a negative regulator. HSF1, HSF2 and HSF4 play a role in transcriptional control of other heat shock proteins. The various HSF proteins share about 40% sequence identity.

HSF1 pathway activity has been implicated in several diseases, including cancer, and autoimmune, and viral diseases. HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g., promyelocytic leukemia), and Hodgkin's disease.

Accordingly, there is need for pharmacologically active agents that are capable of inhibiting HSF1 pathway. Such agents are potentially useful chemotherapeutic agents for the treatment of diseases or conditions in which HSF1 pathway activity is mediated.

SUMMARY OF THE INVENTION

In one aspect, the present invention provides a compound, or a pharmaceutically acceptable salt or solvate thereof, as defined herein.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein, for use in therapy.

In another aspect, the present invention provides a compound as defined herein, or a pharmaceutically acceptable salt or solvate thereof, or a pharmaceutical composition as defined herein, for use in the treatment of HSF1 pathway-mediated conditions or diseases (for example, cancer, autoimmune diseases or viral diseases).

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a HSF1 pathway inhibitory effect.

In another aspect, the present invention provides the use of a compound as defined herein, or a pharmaceutically acceptable salt or solvate thereof, in the manufacture of a medicament for use in treatment of HSF1 pathway-mediated conditions or diseases (for example, cancer, autoimmune diseases or viral diseases).

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of a HSF1 pathway inhibitory effect.

In another aspect, the present invention provides a method of inhibiting HSF1 pathway in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a HSF1 pathway-mediated condition or disease (for example, cancer, autoimmune diseases or viral diseases), in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound as defined herein, or a pharmaceutically acceptable salt or solvate thereof.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicycle [2.2.2]octane, bicycle[2.1.1]hexane, bicycle[1.1.1]pentane and bicyclo[2.2.1]heptyl.

The term "(1-8C)heteroalkyl" refers to an alkyl chain comprising 1-8 carbon atoms which additionally comprises one, two or three heteroatoms present within the alkyl chain which are selected from the group consisting of N, O, or S.

The term "halo" refers to fluoro, chloro, bromo and iodo.

The term "haloalkyl" or "haloalkoxy" is used herein to refer to an alkyl or alkoxy group respectively in which one or more hydrogen atoms have been replaced by halogen (e.g. fluorine) atoms. Examples of haloalkyl and haloalkoxy groups include fluoroalkyl and fluoroalkoxy groups such as —CHF$_2$, —CH$_2$CF$_3$, or perfluoroalkyl/alkoxy groups such as —CF$_3$, —CF$_2$CF$_3$ or —OCF$_3$.

The term "carbocyclyl", "carbocyclic" or "carbocycle" means a non-aromatic saturated or partially saturated monocyclic, or a fused, bridged, or spiro bicyclic carbocyclic ring system(s). Monocyclic carbocyclic rings contain from about 3 to 12 (suitably from 3 to 7) ring atoms. Bicyclic carbocycles contain from 7 to 17 carbon atoms in the rings, suitably 7 to 12 carbon atoms, in the rings. Bicyclic carbocyclic rings may be fused, spiro, or bridged ring systems.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO$_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen. Suitably, the term "heterocyclyl", "heterocyclic" or "heterocycle" will refer to 4, 5, 6 or 7 membered monocyclic rings as defined above.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes and 2-oxa-6-azaspiro[3.3]heptanes.

"Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Suitably, the term "heteroaryl" or "heteroaromatic" will refer to 5 or 6 membered monocyclic hetyeroaryl rings as defined above.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
   a) a benzene ring fused to a 5- or 6-membered ring containing 1, 2 or 3 ring heteroatoms;
   b) a pyridine ring fused to a 5- or 6-membered ring containing 1, 2 or 3 ring heteroatoms;
   c) a pyrimidine ring fused to a 5- or 6-membered ring containing 1 or 2 ring heteroatoms;
   d) a pyrrole ring fused to a 5- or 6-membered ring containing 1, 2 or 3 ring heteroatoms;
   e) a pyrazole ring fused to a 5- or 6-membered ring containing 1 or 2 ring heteroatoms;
   f) a pyrazine ring fused to a 5- or 6-membered ring containing 1 or 2 ring heteroatoms;
   g) an imidazole ring fused to a 5- or 6-membered ring containing 1 or 2 ring heteroatoms;
   h) an oxazole ring fused to a 5- or 6-membered ring containing 1 or 2 ring heteroatoms;
   i) an isoxazole ring fused to a 5- or 6-membered ring containing 1 or 2 ring heteroatoms;
   j) a thiazole ring fused to a 5- or 6-membered ring containing 1 or 2 ring heteroatoms;
   k) an isothiazole ring fused to a 5- or 6-membered ring containing 1 or 2 ring heteroatoms;
   l) a thiophene ring fused to a 5- or 6-membered ring containing 1, 2 or 3 ring heteroatoms;
   m) a furan ring fused to a 5- or 6-membered ring containing 1, 2 or 3 ring heteroatoms;
   n) a cyclohexyl ring fused to a 5- or 6-membered heteroaromatic ring containing 1, 2 or 3 ring heteroatoms; and
   o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl or naphthyl, especially phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention provides a compound of formula I shown below:

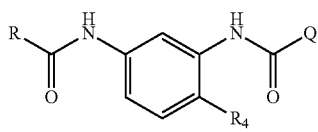
I wherein:
R is a group of the formula:

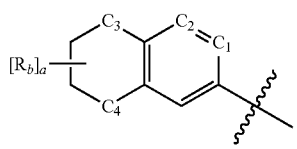
Ia

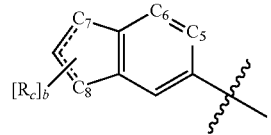
Ib

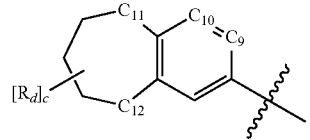
Ic wherein:
$C_1$ is selected from N or $CR_{a1}$;
$C_2$ is selected from N or $CR_{a2}$;
$R_{a1}$ and $R_{a2}$ are each independently selected from hydrogen, fluoro, chloro, cyano, (1-2C)alkyl, (1-2C)alkoxy or (1-2C)haloalkyl;
$C_3$ is selected from O or CH;
$C_4$ is selected from O or CH;
a is 0, 1 or 2;
$R_b$ is selected from fluoro or (1-2C)alkyl;
subject to the proviso that:
 (i) only one of $C_1$ or $C_2$ can be N;
 (ii) one or two of $C_3$ or $C_4$ are oxygen; and
 (iii) when $C_3$ and $C_4$ are both oxygen then a is 1 or 2;
$C_5$ is selected from N or $CR_a$s;
$C_6$ is selected from N or $CR_{a6}$;
$R_{a5}$ and $R_{a6}$ are each independently selected from hydrogen, fluoro, chloro, cyano, (1-2C)alkyl, (1-2C)alkoxy or (1-2C)haloalkyl;
$C_7$ is selected from O or CH;
$C_8$ is selected from O or CH;
b is 0, 1 or 2;
$R_c$ is selected from fluoro or (1-2C)alkyl;
subject to the proviso that:
 (i) only one of $C_5$ or $C_6$ can be N; and
 (ii) one or both of $C_7$ or $C_8$ is O;
$C_9$ is selected from N or $CR_{a9}$;
$C_{10}$ is selected from N or $CR_{a10}$;
$R_{a9}$ and $R_{a10}$ are each independently selected from hydrogen, fluoro, chloro, cyano, (1-2C)alkyl, (1-2C)alkoxy or (1-2C)haloalkyl;
$C_{11}$ is selected from O or CH;
$C_{12}$ is selected from O or CH;
c is 0, 1, 2 or 3;
$R_d$ is selected from fluoro or (1-2C)alkyl;
subject to the proviso that:
 (i) only one of $C_9$ or $C_{10}$ can be N; and
 (ii) one or both of $C_{11}$ and $C_{12}$ is/are oxygen;
$R_4$ is selected from hydrogen, fluoro, chloro, bromo, iodo, $CF_3$, $OCF_3$, cyano, $NO_2$, (1-4C)alkyl, (1-4C)alkoxy, or a group of the formula:

W—X—Y—Z wherein
W is absent or (1-3C)alkylene;
X is —O— or —N($R^{40}$)—, wherein $R^{40}$ is selected from hydrogen or (1-2C)alkyl;
Y is absent or a (1-3C)alkylene;
Z is hydrogen, (1-6C)alkyl, (3-6C)cycloalkyl or a 4 to 10-membered monocyclic or bicyclic heterocyclic ring;

or Y and Z are linked with $R^{40}$ such that, together with the nitrogen atom to which they are attached, they form 4 to 10-membered monocyclic or bicyclic heterocyclic ring;

and wherein any alkylene, alkyl, cycloalkyl or heterocyclyl group present in a $R_4$ substituent group is optionally further substituted by one or more substituent groups independently selected from oxo, halo, nitro, hydroxy, cyano, carboxy, $-M-NR^{41}R^{42}$, $-M-S(O)_dR^{41}$, $-M-C(O)NR^{41}R^{42}$, $-M-NR^{41}C(O)R^{42}$, $-M-NR^{41}S(O)_2R^{42}$, $-M-S(O)_2NR^{41}R^{42}$, (1-5C)alkyl, (1-5C)alkoxy, (1-5C)haloalkyl, (1-5C)haloalkoxy or (1-5C)alkanoyl, and wherein M is absent or (1-4C) alkylene, and $R^{41}$ and $R^{42}$ are each independently selected from hydrogen or (1-5C)alkyl; or $R^{41}$ and $R^{42}$ can be linked such that, together with the nitrogen atom to which they are attached, they form a 4-6 membered heterocyclic ring;

Q is selected from a group of formula II:

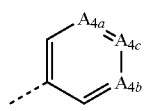

II wherein $A_{4a}$ and $A_{4b}$ are each independently selected from N or $CR_9$, wherein each $R_9$ present is independently selected from hydrogen, halo, cyano, nitro, hydroxy, $NR^dR^e$, (1-3C)alkyl, (1-3C)alkoxy, 5 or 6-membered heteroaryl, or 5 or 6 membered heterocyclyl; wherein $R^d$ and $R^e$ are each independently selected from hydrogen or (1-3C)alkyl; and wherein any (1-3C)alkyl, (1-3C) alkoxy, 5 or 6-membered heteroaryl, or 5 or 6 membered heterocyclyl group present in a $R_9$ substituent group is optionally substituted by one or more substituents selected from halo, cyano, nitro, hydroxy, $NR^fR^g$ or (1-3C)alkoxy, wherein $R^f$ and $R^g$ are each independently selected from hydrogen or (1-3C)alkyl;

$A_{4c}$ is N or $CR_{10}$;

$R_{10}$ is selected from hydrogen, halo, amino, cyano, nitro, hydroxy or a group

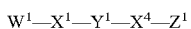

wherein $W^1$ is absent or a linker group of the formula $-[CR^hR^i]_p-$ in which p is an integer selected from 1, 2, 3 or 4, and $R^h$ and $R^i$ are each independently selected from hydrogen or (1-2C)alkyl;

$X^1$ is absent or $-O-$, $-C(O)-$, $-C(O)O-$, $-OC(O)-$, $-CH(OR^j)-$, $-N(R^j)-$, $-N(R^j)-C(O)-$, $-N(R^j)-C(O)O-$, $-C(O)-N(R^j)-$, $-N(R^j)C(O)N(R^j)-$, $-S-$, $-SO-$, $-SO_2-$, $-S(O)_2N(R^j)-$, or $-N(R^j)SO_2-$ wherein $R^j$ is selected from hydrogen or methyl;

$Y^1$ is absent or a linker group of the formula $-[CR^kR^l]_q-$ in which q is an integer selected from 1, 2, 3 or 4, and $R^k$ and $R^l$ are each independently selected from hydrogen or (1-2C)alkyl;

$X^4$ is absent or $-O-$, $-C(O)-$, $-C(O)O-$, $-OC(O)-$, $-CH(OR^j)-$, $-N(R^j)-$, $-N(R^j)-C(O)-$, $-N(R^j)-C(O)O-$, $-C(O)-N(R^j)-$, $-N(R^j)C(O)N(R^j)-$, $-S-$, $-SO-$, $-SO_2-$, $-S(O)_2N(R^j)-$, or $-N(R^j)SO_2-$ wherein $R^j$ is selected from hydrogen or methyl; and $Z^1$ is (1-6C)alkyl, (2-6C)alkenyl, (2-6C)alkynyl, aryl, (3-6C)cycloalkyl, (3-6C)cycloalkenyl, heteroaryl or heterocyclyl;

and wherein $Z^1$ is optionally further substituted by one or more substituent groups independently selected from oxo, halo, cyano, nitro, hydroxy, carboxy, $NR^mR^n$, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, $C(O)NR^mR^n$, $NR^mC(O)R^n$, $NR^mS(O)_2R^n$ and $S(O)_2NR^mR^n$;

wherein $R^m$ and $R^n$ are each independently selected from hydrogen, (1-4C)alkyl or (3-6C)cycloalkyl or (3-6C)cycloalkyl(1-2C)alkyl; or $R^m$ and $R^n$ can be linked such that, together with the nitrogen atom to which they are attached, they form a 4-6 membered heterocyclic ring; and wherein any alkyl, aryl, heterocyclyl or heteroaryl group present in a substituent group on $Z^1$ is optionally further substituted by halo, cyano, nitro, hydroxy, caboxy, $NR^oR^p$, (1-2C) alkoxy, or (1-2C)alkyl;

wherein $R^o$ and $R^p$ are selected from hydrogen or (1-2C)alkyl;

or Q is a group of formula III:

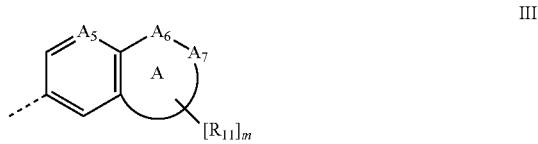

III wherein $A_5$ is selected from N or $CR_5$, where $R_5$ is selected from hydrogen, halo, cyano, nitro, hydroxy, $NR^qR^u$, (1-3C) alkyl, (1-3C)alkoxy, 5 or 6-membered heteroaryl, or 5 or 6 membered heterocyclyl; wherein $R^q$ and $R^u$ are each independently selected from hydrogen or (1-3C) alkyl, and wherein any (1-3C)alkyl, (1-3C)alkoxy, 5 or 6-membered heteraryl, or 5 or 6 membered heterocyclyl group present in a $R_5$ substituent group is optionally substituted by one or more substitutents selected from halo, cyano, nitro, hydroxy, $NR^vR^w$, or (1-3C) alkoxy, wherein $R^v$ and $R^w$ are each independently selected from hydrogen or (1-3C)alkyl;

Ring A is:
 a fused phenyl ring;
 a fused 5 or 6 membered carbocyclic ring;
 a fused 5 or 6 membered heteroaryl ring comprising one or two heteroatoms independently from N, S or O; or
 a fused 5, 6 or 7-membered heterocyclic ring comprising one or two heteroatoms independently from N, S or O;

$A_6$ is selected from N, O, S, S(O), $S(O)_2$, $CR_6$, $C(R_6)_2$, $NR_{60}$, where $R_6$ is selected from hydrogen, oxo, fluoro, chloro, (1-2C)alkyl, (1-2C)alkoxy, (1-2C)haloalkoxy or (1-2C)haloalkyl and $R_{60}$ is hydrogen, $O^-$, (1-6C) alkyl, $-C(O)-R_{61}$, $-C(O)O-R_{61}$, or $-C(O)N(R_{62})$ $R_{61}$, wherein $R_{61}$ is selected from hydrogen, (1-6C) alkyl, (3-6C)cycloalkyl, aryl, heteroaryl or heterocyclyl and $R_{62}$ is selected from hydrogen or (1-3C)alkyl;

A₇ is selected from N, O, CR₇, S, S(O), S(O)₂, C(R₇)₂, NR₇₀, where R₇₀ is hydrogen, O⁻, (1-6C)alkyl, —C(O)—R₇₁, —C(O)O—R₇₁, or —C(O)N(R₇₂)R₇₁, wherein
R₇₁ is selected from hydrogen, (1-6C)alkyl, (3-6C)cycloalkyl, aryl, heteroaryl or heterocyclyl and R₇₂ is selected from hydrogen or (1-3C)alkyl;
m is 0, 1 or 2;
R₇ and R₁₁ are each independently halo, cyano, oxo, or a group
W²—X²—Y²—X³—Z²
wherein
W² is absent or a linker group of the formula —[CR^xR^y]ᵣ— in which r is an integer selected from 1, 2, 3 or 4, and R^x and R^y are each independently selected from hydrogen or (1-2C)alkyl;
X² is absent, —O—, —C(O)—, —C(O)O—, —OC(O)—, —CH(OR^z)—, —N(R^z)—, —N(R^z)—C(O)—, —N(R^z)—C(O)O—, —C(O)—N(R^z)—, —N(R^z)C(O)N(R^z)—, —S—, —SO—, —SO₂—, —S(O)₂N(R^z)—, or —N(R^z)SO₂, wherein R^z is selected from hydrogen or methyl;
Y² is absent or a linker group of the formula —[CR^aaR^bb]ₛ— in which s is an integer selected from 1, 2, 3 or 4, and R^aa and R^bb are each independently selected from hydrogen or (1-2C)alkyl;
X³ is absent, —O—, —C(O)—, —C(O)O—, —OC(O)—, —CH(OR^cc)—, —N(R^cc)—, —N(R^cc)—C(O)—, —N(R^cc)—C(O)O—, —C(O)—N(R^cc)—, —N(R^cc)C(O)N(R^cc)—, —S—, —SO—, —SO₂—, —S(O)₂N(R^cc)—, or —N(R^cc)SO₂, wherein R^cc is selected from hydrogen or methyl; and
Z² is hydrogen, (1-6C)alkyl, (2-6C)alkenyl, (2-6C)alkynyl, aryl, (3-6C)cycloalkyl, (3-6C)cycloalkenyl, heteroaryl, or heterocyclyl,
and wherein Z² is optionally further substituted by one or more substituent groups independently selected from oxo, halo, cyano, nitro, hydroxy, caboxy, NR^ddR^ee, (1-4C)alkoxy, (1-4C)alkyl, (3-8C)cycloalkyl, (3-8C)cycloalkyl-(1-3C)alkyl, (1-4C)alkanoyl, (1-4C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR^ddR^ee, NR^ddC(O)R^ee, NR^ddSO₂R^ee and SO₂NR^ddR^ee; wherein R^dd and R^ee are each independently selected from hydrogen, (1-4C)alkyl, (3-6C)cycloalkyl or (3-6C)cycloalkyl(1-2C)alkyl; or R^dd and R^ee can be linked such that, together with the nitrogen atom to which they are attached, they form a 4-6 membered heterocyclic ring;
and wherein any alkyl, aryl, heterocyclyl or heteroaryl group present in a substituent group on Z² is optionally further substituted by halo, cyano, nitro, hydroxy, caboxy, NR^ffR^gg, (1-2C)alkoxy, or (1-2C)alkyl; wherein R^ff and R^gg are selected from hydrogen or (1-2C)alkyl;
or a pharmaceutically acceptable salt or solvate thereof.

In one embodiment of the first aspect the following provisos apply (i) when R₄ is methyl, and Q is

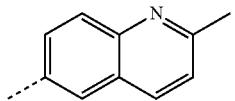

then R is not

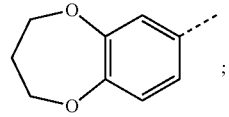

(ii) when R₄ is hydrogen, and Q is

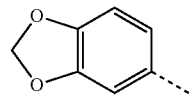

then R is not

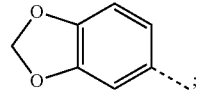

(iii) when R₄ is fluoro, and Q is

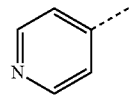

then R is not

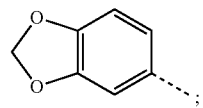

(iv) when R₄ is hydrogen, and Q is

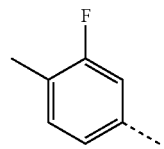

then R is not

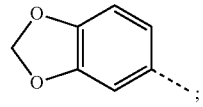

and (v) when $R_4$ is hydrogen, and Q is

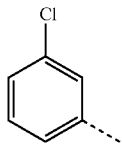

then R is not

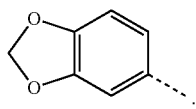

The ring A fused ring systems shown in Formula III are made up of two carbon atoms from adjacent fused ring, the atoms $A_6$ and $A_7$ and either one, two or three additional ring atoms that link $A_7$ to the fused ring (depending on whether ring A is a fused 5, 6 or 7 membered ring respectively). For the avoidance of doubt, when m is 1 or 2 then each $R_{11}$ group present resides on the one, two or three additional ring atoms that are present in Ring A (i.e. they are not present on atoms $A_6$ and $A_7$).

Particular compounds of the invention include, for example, compounds of the formula I, or pharmaceutically acceptable salts or solvates thereof, wherein, unless otherwise stated, each of R, $C_1$, $C_2$, $C_3$, $C_4$, $C_5$, $C_6$, $C_7$, $C_8$, $C_9$, $C_{10}$, $C_{11}$, $C_{12}$, $R_c$, $R_c$, $R_d$, $R_{a1}$, $R_{a2}$, a, b, c, $R_4$, Q, $A_{4a}$, $A_{4b}$, $A_{4c}$, $R_{10}$, $A_5$, ring A, $A_6$, $A_7$, $R_7$, m and $R_{11}$ has any of the meanings defined hereinbefore or in any one of paragraphs (1) to (103) hereinafter:—

(1) R is a group of the formula:

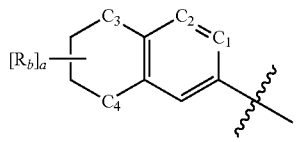

Ia as defined herein;

(2) R is a group of the formula:

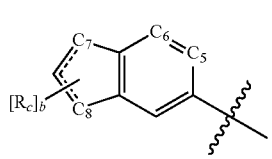

Ib as defined herein;

(3) R is a group of the formula:

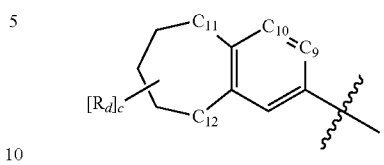

Ic as defined herein;

(4) R is selected from the group consisting of:

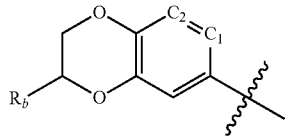

Ia1

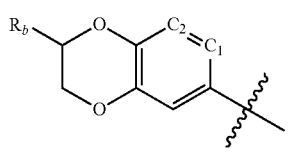

Ia2

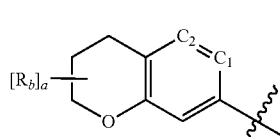

Ia3

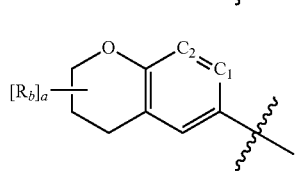

Ia4

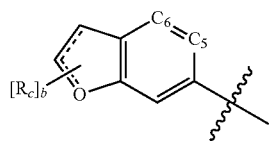

Ib1

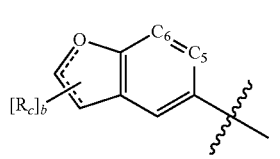

Ib2

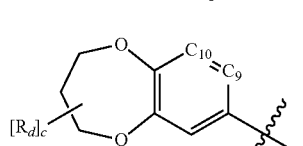

Ic1

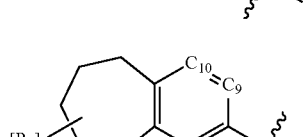

Ic2

-continued

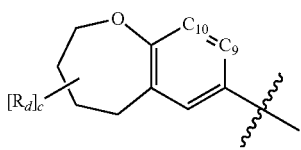
Ic3

(5) wherein $C_1$, $C_2$, $C_5$, $C_6$, $C_9$, $C_{10}$, $R_b$, $R_c$, $R_d$, a, b and c each have any one of the definitions set out herein. R is selected group consisting of:

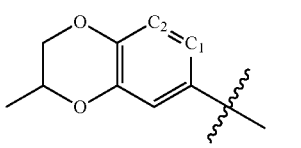

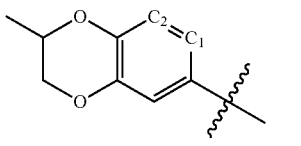

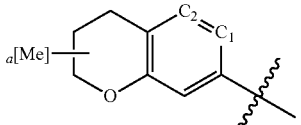

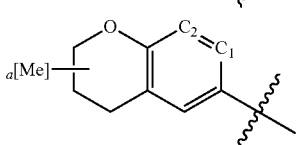

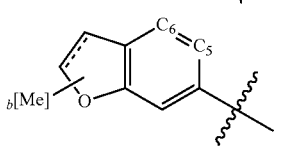

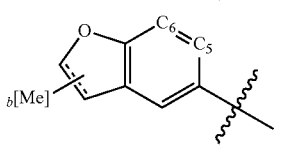

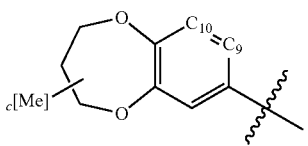

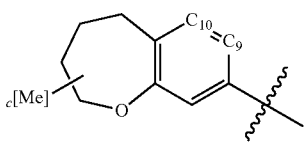

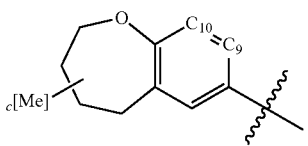

wherein $C_1$, $C_2$, $C_5$, $C_6$, $C_9$, $C_{10}$, a, b and c each have any one of the definitions set out herein;

(6) R is selected from the group consisting of:

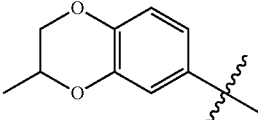

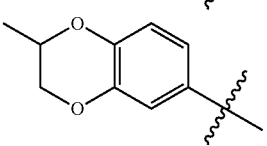

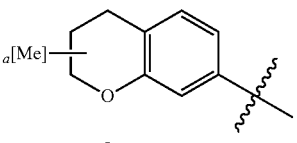

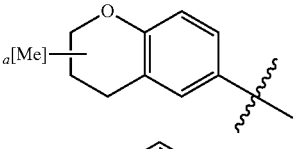

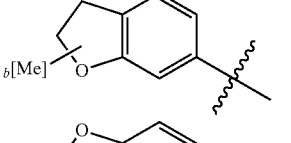

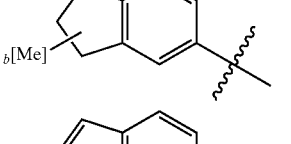

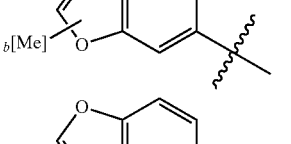

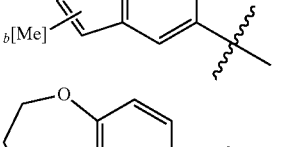

wherein a and b each have any one of the definitions set out herein.
(7) $C_1$ is N;
(8) $C_1$ is $CR_{a1}$;
(9) $C_1$ is $CR_{a1}$ wherein $R_{a1}$ is selected from hydrogen, fluoro, chloro, cyano, methyl, methoxy, —$CF_3$ or —$OCF_3$;
(10) $C_1$ is $CR_{a1}$ wherein $R_{a1}$ is selected from hydrogen or fluoro;
(11) $C_1$ is $CR_{a1}$ wherein $R_{a1}$ is hydrogen;
(12) $C_2$ is N;
(13) $C_2$ is $CR_{a2}$;
(14) $C_2$ is $CR_{a2}$ wherein $R_{a2}$ is selected from hydrogen, fluoro, chloro, cyano, methyl, methoxy, —$CF_3$ or —$OCF_3$;
(15) $C_2$ is $CR_{a2}$ wherein $R_{a2}$ is selected from hydrogen or fluoro;
(16) $C_2$ is $CR_{a2}$ wherein $R_{a2}$ is hydrogen;

(17) $C_3$ is O;
(18) $C_3$ is CH;
(19) $C_4$ is O;
(20) $C_4$ is CH;
(21) a is 0 or 1;
(22) a is 0;
(23) a is 1;
(24) $R_b$ is selected from fluoro or methyl;
(25) $R_b$ is methyl;
(26) $C_5$ is N;
(27) $C_5$ is $CR_{a5}$;
(28) $C_5$ is $CR_{a5}$ wherein $R_{a5}$ is selected from hydrogen, fluoro, chloro, cyano, methyl, methoxy, —$CF_3$ or —$OCF_3$;
(29) $C_5$ is $CR_{a5}$ wherein $R_{a5}$ is selected from hydrogen or fluoro;
(30) $C_5$ is $CR_{a5}$ wherein $R_{a5}$ is hydrogen;
(31) $C_6$ is N;
(32) $C_6$ is $CR_{a6}$;
(33) $C_6$ is $CR_{a6}$ wherein $R_{a6}$ is selected from hydrogen, fluoro, chloro, cyano, methyl, methoxy, —$CF_3$ or —$OCF_3$;
(34) $C_6$ is $CR_{a6}$ wherein $R_{a6}$ is selected from hydrogen or fluoro;
(35) $C_6$ is $CR_{a6}$ wherein $R_{a6}$ is hydrogen;
(36) $C_7$ is O;
(37) $C_7$ is CH;
(38) $C_8$ is O;
(39) $C_8$ is CH;
(40) b is 0 or 1;
(41) b is 0;
(42) $R_c$ is selected from fluoro or methyl;
(43) $R_c$ is methyl;
(44) $C_9$ is N;
(45) $C_9$ is $CR_{a9}$;
(46) $C_9$ is $CR_{a9}$ wherein $R_{a9}$ is selected from hydrogen, fluoro, chloro, cyano, methyl, methoxy, —$CF_3$ or —$OCF_3$;
(47) $C_9$ is $CR_{a9}$ wherein $R_{a9}$ is selected from hydrogen or fluoro;
(48) $C_9$ is $CR_{a9}$ wherein $R_{a9}$ is hydrogen;
(49) $C_{10}$ is N;
(50) $C_{10}$ is $CR_{a10}$;
(51) $C_{10}$ is $CR_{a10}$ wherein $R_{a10}$ is selected from hydrogen, fluoro, chloro, cyano, methyl, methoxy, —$CF_3$ or —$OCF_3$;
(52) $C_{10}$ is $CR_{a10}$ wherein $R_{a10}$ is selected from hydrogen or fluoro;
(53) $C_{10}$ is $CR_{a10}$ wherein $R_{a10}$ is hydrogen;
(54) $C_{11}$ O;
(55) $C_{11}$ is CH;
(56) $C_{12}$ is O;
(57) $C_{12}$ is CH;
(58) c is 0, 1, or 2;
(59) c is 0 or 1;
(60) c is 0;
(61) $R_d$ is selected from fluoro or (1-2C)alkyl;
(62) $R_d$ is selected from fluoro or methyl;
(63) $R_d$ is methyl;
(64) $R_4$ is selected from hydrogen, fluoro, chloro, bromo, iodo, $CF_3$, $OCF_3$, cyano, (1-4C)alkyl, (1-4C)alkoxy, or a group of the formula:

W—X—Y—Z wherein
W is absent or (1-3C)alkylene;
X is —O— or —N($R^{40}$)—, wherein $R^{40}$ is selected from hydrogen or (1-2C)alkyl;
Y is absent or a (1-3C)alkylene;
Z is hydrogen, (1-6C)alkyl, (3-6C)cycloalkyl or a 4 to 10-membered monocyclic or bicyclic heterocyclic ring;
or Y and Z are linked with $R^{40}$ such that, together with the nitrogen atom to which they are attached, they form 4 to 10-membered monocyclic or bicyclic heterocyclic ring optionally comprising one or two further heteroatoms selected from N, O or S;
and wherein any alkylene, alkyl, cycloalkyl or heterocyclyl group present in a $R_4$ substituent group is optionally further substituted by one or more substituent groups independently selected from halo, hydroxy, cyano, -M-$NR^{41}R^{42}$, -M-S(O)$_d R^{41}$, (1-5C)alkyl, (1-5C)alkoxy, (1-5C)haloalkyl or (1-5C)haloalkoxy, and wherein M is absent or (1-4C)alkylene, and $R^{41}$ and $R^{42}$ are each independently selected from hydrogen or (1-5C)alkyl;
(65) $R_4$ is selected from hydrogen, fluoro, chloro, $CF_3$, $OCF_3$, cyano, (1-4C)alkyl, (1-4C)alkoxy, or a group of the formula:

W—X—Y—Z wherein
W is absent or (1-3C)alkylene;
X is —O— or —N($R^{40}$)—, wherein $R^{40}$ is selected from hydrogen or (1-2C)alkyl;
Y is absent or a (1-3C)alkylene;
Z is hydrogen, (1-6C)alkyl, (3-6C)cycloalkyl or a 4 to 10-membered monocyclic or bicyclic heterocyclic ring;
or Y and Z are linked with $R^{40}$ such that, together with the nitrogen atom to which they are attached, they form 4 to 10-membered monocyclic or bicyclic heterocyclic ring optionally comprising one or two further heteroatoms selected from N, O or S;
and wherein any alkylene, alkyl, cycloalkyl or heterocyclyl group present in a $R_4$ substituent group is optionally further substituted by one or more substituent groups independently selected from halo, hydroxy, cyano, -M-$NR^{41}R^{42}$, -M-S(O)$_d R^{41}$, (1-5C)alkyl, (1-5C)alkoxy, (1-5C)haloalkyl or (1-5C)haloalkoxy, and wherein M is absent or (1-4C)alkylene, and $R^{41}$ and $R^{42}$ are each independently selected from hydrogen or (1-5C)alkyl;
(66) $R_4$ is selected from hydrogen, fluoro, chloro, $CF_3$, $OCF_3$, cyano, (1-4C)alkyl, (1-4C)alkoxy, or a group of the formula:

W—X—Y—Z wherein
W is absent or (1-3C)alkylene;
X is —N($R^{40}$)—, wherein $R^{40}$ is selected from hydrogen or (1-2C)alkyl; and Y and Z are linked with $R^{40}$ such that, together with the nitrogen atom to which they are attached, they form 4 to 10-membered monocyclic or bicyclic heterocyclic ring optionally comprising one or two further heteroatoms selected from N, O or S;
and wherein any alkylene, alkyl, cycloalkyl or heterocyclyl group present in a $R_4$ substituent group is optionally further substituted by one or more substituent groups independently selected from halo, hydroxy, cyano, -M-$NR^{41}R^{42}$, -M-S(O)$_d R^{41}$, (1-5C)alkyl, (1-5C)alkoxy, (1-5C)haloalkyl or (1-5C)haloalkoxy, and wherein M is absent or (1-4C)alkylene, and $R^{41}$ and $R^{42}$ are each independently selected from hydrogen or (1-5C)alkyl;

(67) R₄ is selected from hydrogen, fluoro, chloro, CF₃, OCF₃, cyano, (1-4C)alkyl, (1-4C)alkoxy, or a group of the formula:

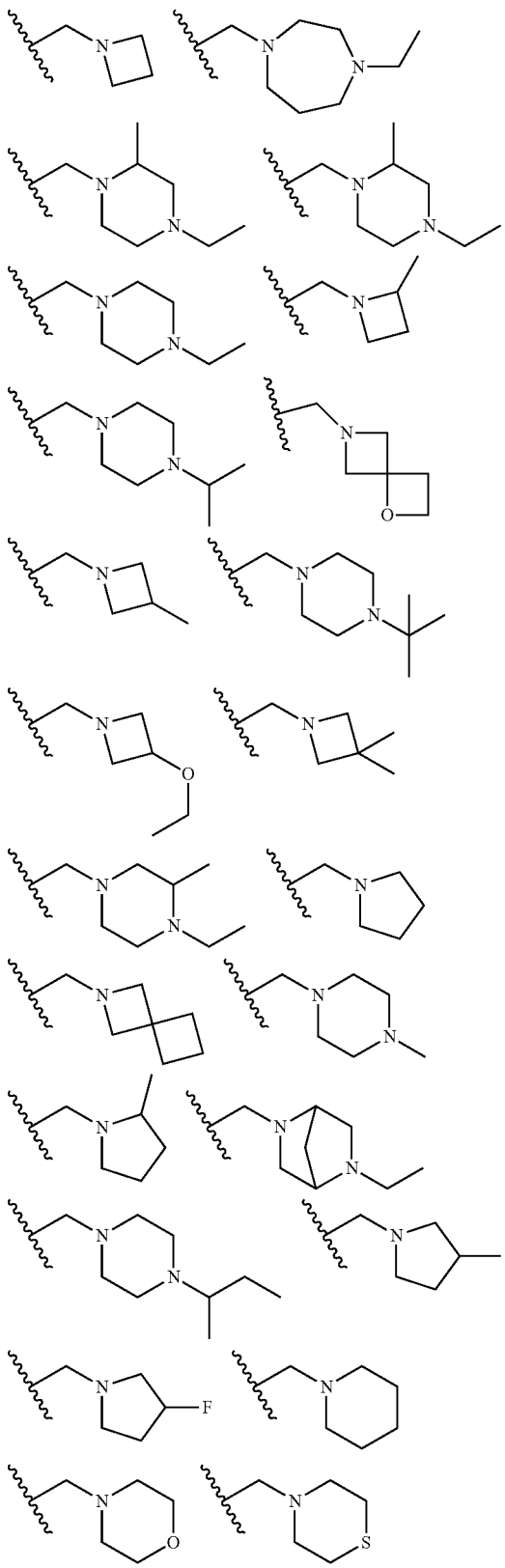

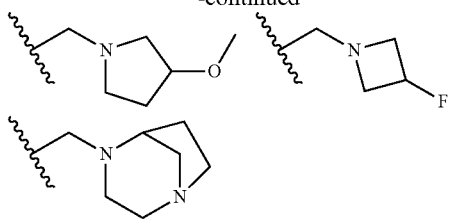

(68) Q is selected from a group of formula II:

wherein $A_{4a}$ and $A_{4b}$ are each independently selected from N or $CR_9$, wherein $R_9$ is selected from hydrogen, halo, cyano, nitro, hydroxy, $NR^d R^e$, (1-3C)alkyl, (1-3C)alkoxy, 5 or 6-membered heteroaryl, or 5 or 6 membered heterocyclyl; wherein $R^d$ and $R^e$ are each independently selected from hydrogen or (1-3C)alkyl;

and wherein any (1-3C)alkyl, (1-3C)alkoxy, 5 or 6-membered heteroaryl, or 5 or 6 membered heterocyclyl group present in a $R_9$ substituent group is optionally substituted by one or more substituents selected from halo, cyano, hydroxy, $NR^f R^g$ or (1-3C)alkoxy, wherein $R^f$ and $R^g$ are each independently selected from hydrogen or (1-2C)alkyl;

$A_{4c}$ is N or $CR_{10}$;

$R_{10}$ is selected from hydrogen, halo, amino, cyano, nitro, hydroxy or a group $$W^1—X^1—Y^1—X^4—Z^1$$

wherein $W^1$ is absent or a linker group of the formula —$[CR^h R^i]_p$— in which p is an integer selected from 1 or 2, and $R^h$ and $R^i$ are each independently selected from hydrogen or methyl;

$X^1$ is absent or —O—, —C(O)—, —C(O)O—, —OC(O)—, —CH(OR$^j$)—, —N(R$^j$)—, —N(R$^j$)—C(O)—, —N(R$^j$)—C(O)O—, —C(O)—N(R$^j$)—, —S—, —SO—, —SO₂—, —S(O)₂N(R$^j$)—, or —N(R$^j$)SO₂— wherein R$^j$ is selected from hydrogen or methyl;

$Y^1$ is absent or a linker group of the formula —$[CR^k R^l]_q$— in which q is an integer selected from 1, 2, 3 or 4, and $R^k$ and $R^l$ are each independently selected from hydrogen or (1-2C)alkyl;

$X^4$ is absent or —O—, —C(O)—, —C(O)O—, —OC(O)—, —CH(OR$^j$)—, —N(R$^j$)—, —N(R$^j$)—C(O)—, —N(R$^j$)—C(O)O—, —C(O)—N(R$^j$)—, —S—, —SO—, —SO₂—, —S(O)₂N(R$^j$)—, or —N(R$^j$)SO₂— wherein R$^j$ is selected from hydrogen or methyl; and $Z^1$ is (1-6C)alkyl, aryl, heteroaryl or heterocyclyl;

and wherein $Z^1$ is optionally further substituted by one or more substituent groups independently selected from oxo, halo, cyano, hydroxy, caboxy, $NR^m R^n$, (1-2C)alkoxy, (1-2C)alkyl, (3-6C)cycloalkyl, (3-6C)cycloalkyl-(1-2C)alkyl, (1-2C)alkanoyl, (1-2C)alkylsulphonyl, aryl, aryloxy, heterocyclyl, heterocyclyloxy, heterocyclyl-(1-2C) alkyl, heteroaryl, heteroaryloxy, heteroaryl-(1-2C) alkyl, C(O)NR'''R'', NR'''C(O)R'', NR'''S(O)$_2$R'' and S(O)$_2$NR'''R''; wherein R''' and R'' are each independently selected from hydrogen or (1-4C) alkyl; or R''' and R'' can be linked such that, together with the nitrogen atom to which they are attached, they form a 4-6 membered heterocyclic ring;

and wherein any alkyl, aryl, heterocyclyl or heteroaryl group present in a substituent group on $Z^1$ is optionally further substituted by halo, cyano, hydroxy, NR$^o$R$^p$, (1-2C)alkoxy, or (1-2C)alkyl; wherein R$^o$ and R$^p$ are selected from hydrogen or (1-2C)alkyl;

or Q is a group of formula III:

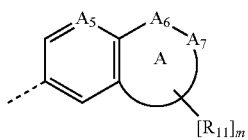

III wherein $A_5$ is selected from N or CR$_5$, where R$_5$ is selected from hydrogen, halo, cyano, hydroxy, NR$^q$R$^u$, (1-3C)alkyl, (1-3C)alkoxy, 5 or 6-membered heteroaryl, or 5 or 6 membered heterocyclyl; wherein R$^q$ and R$^u$ are each independently selected from hydrogen or (1-3C)alkyl;

and wherein any (1-3C)alkyl, (1-3C)alkoxy, 5 or 6-membered heteraryl, or 5 or 6 membered heterocyclyl group present in a R$_5$ substituent group is optionally substituted by one or more substitutents selected from halo, cyano, nitro, hydroxy, NR$^v$R$^w$, or (1-3C)alkoxy, wherein R$^v$ and R$^w$ are each independently selected from hydrogen or (1-3C)alkyl;

Ring A is:
 a fused phenyl ring;
 a fused 5 or 6 membered carbocyclic ring;
 a fused 5 or 6 membered heteroaryl ring comprising one or two heteroatoms independently from N, S or O; or
 a fused 5, 6 or 7-membered heterocyclic ring comprising one or two heteroatoms independently from N, S or O;

$A_6$ is selected from N, O, S, S(O)$_2$, CR$_6$, C(R$_6$)$_2$, NR$_{60}$, where R$_6$ is selected from hydrogen, oxo, fluoro, chloro, (1-2C)alkyl, (1-2C)alkoxy, (1-2C)haloalkoxy or (1-2C)haloalkyl and R$_{60}$ is hydrogen, O$^-$, (1-6C)alkyl, —C(O)—R$_{61}$, —C(O)O—R$_{61}$, or —C(O)N(R$_{62}$)R$_{61}$, wherein R$_{61}$ is selected from hydrogen, (1-6C)alkyl, aryl, heteroaryl or heterocyclyl and R$_{62}$ is selected from hydrogen or (1-2C)alkyl;

$A_7$ is selected from N, O, CR$_7$, S, S(O)$_2$, C(R$_7$)$_2$, NR$_{70}$, where R$_{70}$ is hydrogen, O$^-$, (1-6C)alkyl, —C(O)—R$_{71}$, —C(O)O—R$_{71}$, or —C(O)N(R$_{72}$)R$_{71}$, wherein R$_{71}$ is selected from hydrogen, (1-6C)alkyl, aryl, heteroaryl or heterocyclyl and R$_{72}$ is selected from hydrogen or (1-2C)alkyl;

m is 0, 1 or 2;

R$_7$ and R$_{11}$ are each independently halo, cyano, oxo, or a group $W^2$—$X^2$—$Y^2$—$X^3$—$Z^2$ wherein $W^2$ is absent or a linker group of the formula —[CR$^x$R$^y$]$_r$— in which r is an integer selected from 1, 2, 3 or 4, and R$^x$ and R$^y$ are each independently selected from hydrogen or (1-2C)alkyl;

$X^2$ is absent, —O—, —C(O)—, —C(O)O—, —OC(O)—, —CH(OR$^z$)—, —N(R$^z$)—, —N(R$^z$)—C(O)—, —N(R$^z$)—C(O)O—, —C(O)—N(R$^z$)—, —S—, —SO—, —SO$_2$—, —S(O)$_2$N(R$^z$)—, or —N(R$^z$)SO$_2$, wherein R$^z$ is selected from hydrogen or methyl;

$Y^2$ is absent or a linker group of the formula —[CR$^{aa}$R$^{bb}$]$_s$— in which s is an integer selected from 1, 2, 3 or 4, and R$^{aa}$ and R$^{bb}$ are each independently selected from hydrogen or (1-2C)alkyl;

$X^3$ is absent, —O—, —C(O)—, —C(O)O—, —OC(O)—, —CH(OR$^{cc}$)—, —N(R$^{cc}$)—, —N(R$^{cc}$)—C(O)—, —N(R$^{cc}$)—C(O)O—, —C(O)—N(R$^{cc}$)—, —S—, —SO—, —SO$_2$—, —S(O)$_2$N(R$^{cc}$)—, or —N(R$^{cc}$)SO$_2$, wherein R$^{cc}$ is selected from hydrogen or methyl; and $Z^2$ is hydrogen, (1-6C)alkyl, (2-6C)alkenyl, aryl, (3-6C)cycloalkyl, heteroaryl, or heterocyclyl, and wherein $Z^2$ is optionally further substituted by one or more substituent groups independently selected from oxo, halo, cyano, nitro, hydroxy, caboxy, NR$^{dd}$R$^{ee}$, (1-4C)alkoxy, (1-4C)alkyl, (3-8C)cycloalkyl, (1-2C)alkanoyl, (1-2C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$^{dd}$R$^{ee}$, NR$^{dd}$C(O)R$^{ee}$, NR$^{dd}$SO$_2$R$^{ee}$ and SO$_2$NR$^{dd}$R$^{ee}$; wherein R$^{dd}$ and R$^{ee}$ are each independently selected from hydrogen, (1-4C)alkyl, (3-6C)cycloalkyl; or R$^{dd}$ and R$^{ee}$ can be linked such that, together with the nitrogen atom to which they are attached, they form a 4-6 membered heterocyclic ring;

and wherein any alkyl, aryl, heterocyclyl or heteroaryl group present in a substituent group on $Z^2$ is optionally further substituted by halo, cyano, nitro, hydroxy, caboxy, NR$^{ff}$R$^{gg}$, (1-2C)alkoxy, or (1-2C)alkyl; wherein R$^{ff}$ and R$^{gg}$ are selected from hydrogen or (1-2C)alkyl;

(69) Q is a group of formula II as defined herein;

(70) $A_{4a}$ and $A_{4b}$ are each independently selected from N or CR$_9$, wherein R$_9$ is selected from hydrogen, halo, cyano, hydroxy, NR$^d$R$^e$, (1-3C)alkyl, (1-3C)alkoxy, 5 or 6-membered heteroaryl, or 5 or 6 membered heterocyclyl; wherein R$^d$ and R$^e$ are each independently selected from hydrogen or (1-2C)alkyl;

and wherein any (1-3C)alkyl, (1-3C)alkoxy, 5 or 6-membered heteroaryl, or 5 or 6 membered heterocyclyl group present in a R$_9$ substituent group is optionally substituted by one or more substituents selected from halo, cyano, hydroxy, NR$^f$R$^g$ or (1-3C)alkoxy, wherein R$^f$ and R$^g$ are each independently selected from hydrogen or (1-2C)alkyl;

(71) $A_{4a}$ and $A_{4b}$ are each independently selected from N or CR$_9$, wherein R$_9$ is selected from hydrogen, halo, cyano, hydroxy, NR$^d$R$^e$, (1-3C)alkyl, (1-3C)alkoxy, 5 or 6-membered heteroaryl, or 5 or 6 membered heterocyclyl; wherein R$^d$ and R$^e$ are each independently selected from hydrogen or (1-2C)alkyl;

(72) $A_{4a}$ and $A_{4b}$ are CR$_9$ and $A_{4c}$ is CR$_{10}$, or one or two of $A_{4a}$, $A_{4b}$ and $A_{4c}$ are N and the others are CR$_9$ (in the case of $A_{4a}$ and $A_{4b}$) or CR$_{10}$ (in the case of $A_{4c}$);

(73) $A_{4a}$ and $A_{4b}$ are $CR_9$ and $A_{4c}$ is $CR_{10}$, or one of $A_{4a}$, $A_{4b}$ and $A_{4c}$ is N and the others are $CR_9$ (in the case of $A_{4a}$ and $A_{4b}$) or $CR_{10}$ (in the case of $A_{4c}$);

(74) $A_{4a}$ and $A_{4b}$ are both CH;

(75) $A_{4c}$ is N;

(76) $A_{4c}$ is $CR_{10}$;

(77) $R_{10}$ is selected from hydrogen, halo, amino, cyano, hydroxy or a group $$W^1-X^1-Y^1-X^4-Z^1$$

wherein
$W^1$ is absent or a linker group of the formula —[$CR^hR^i$]$_p$— in which p is an integer selected from 1 or 2, and $R^h$ and $R^i$ are hydrogen;
$X^1$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^j$ is selected from hydrogen or methyl;
$Y^1$ is absent or a linker group of the formula qj—[$CR^kR^l$]$_q$— in which q is an integer selected from 1, 2, 3 or 4, and $R^k$ and $R^l$ are each independently selected from hydrogen or methyl;
$X^4$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^j$ is selected from hydrogen or methyl; and
$Z^1$ is (1-6C)alkyl, aryl, heteroaryl or heterocyclyl;
and wherein $Z^1$ is optionally further substituted by one or more substituent groups independently selected from oxo, halo, cyano, hydroxy, caboxy, NR$'''$R$''$, (1-2C)alkoxy, (1-2C)alkyl, (3-6C)cycloalkyl, (1-2C)alkanoyl, (1-2C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$'''$R$''$, NR$'''$C(O)R$''$, NR$'''$S(O)$_2$R$''$ and S(O)$_2$NR$'''$R$''$; wherein R$'''$ and R$''$ are each independently selected from hydrogen or (1-4C)alkyl; or R$'''$ and R$''$ can be linked such that, together with the nitrogen atom to which they are attached, they form a 4-6 membered heterocyclic ring;
and wherein any alkyl, aryl, heterocyclyl or heteroaryl group present in a substituent group on $Z^1$ is optionally further substituted by halo, cyano, hydroxy, NR$^o$R$^p$, (1-2C)alkoxy, or (1-2C)alkyl; wherein R$^o$ and R$^p$ are selected from hydrogen or (1-2C)alkyl;

(78) $R_{10}$ is selected from hydrogen, halo, amino, cyano, hydroxy or a group $$W^1-X^1-Y^1-X^4-Z^1$$

wherein
$W^1$ is absent;
$X^1$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^j$ is selected from hydrogen or methyl;
$Y^1$ is absent or a linker group of the formula —[$CR^kR^l$]$_q$— in which q is an integer selected from 1, 2, 3 or 4, and $R^k$ and $R^l$ are hydrogen;
$X^4$ is absent or —O—, —C(O)—, —C(O)O—, —OC(O)—, —N(R$^j$)—, —N(R$^j$)—C(O)—, —N(R$^j$)—C(O)O—, —C(O)—N(R$^j$)—, —S—, —SO—, —SO$_2$—, —S(O)$_2$N(R$^j$)—, or —N(R$^j$)SO$_2$— wherein R$^j$ is selected from hydrogen or methyl; and
$Z^1$ is (1-6C)alkyl, aryl, heteroaryl or heterocyclyl;
and wherein $Z^1$ is optionally further substituted by one or more substituent groups independently selected from oxo, halo, cyano, hydroxy, NR$'''$R$''$, (1-2C)alkoxy, (1-2C)alkyl, (3-6C)cycloalkyl, (1-2C)alkanoyl, (1-2C)alkylsulphonyl, aryl, aryloxy, heterocyclyl, heterocyclyloxy, heterocyclyl-(1-2C)alkyl, heteroaryl, heteroaryloxy, heteroaryl-(1-2C)alkyl, C(O)NR$'''$R$''$, NR$'''$C(O)R$''$, NR$'''$S(O)$_2$R$''$ and S(O)$_2$NR$'''$R$''$; wherein R$'''$ and R$''$ are each independently selected from hydrogen or (1-4C)alkyl; or R$'''$ and R$''$ can be linked such that, together with the nitrogen atom to which they are attached, they form a 4-6 membered heterocyclic ring;
and wherein any alkyl, aryl, heterocyclyl or heteroaryl group present in a substituent group on $Z^1$ is optionally further substituted by halo, cyano, hydroxy, NR$^o$R$^p$, (1-2C)alkoxy, or (1-2C)alkyl; wherein R$^o$ and R$^p$ are selected from hydrogen or (1-2C)alkyl;

(79) $A_5$ is selected from N or $CR_5$, where $R_5$ is selected from hydrogen, halo, cyano, hydroxy, NR$^q$R$^u$, (1-3C)alkyl, (1-3C)alkoxy, 5 or 6-membered heteroaryl, or 5 or 6 membered heterocyclyl; wherein R$^q$ and R$^u$ are each independently selected from hydrogen or (1-3C)alkyl; and wherein any (1-3C)alkyl, (1-3C)alkoxy, 5 or 6-membered heteraryl, or 5 or 6 membered heterocyclyl group present in a $R_5$ substituent group is optionally substituted by one or more substitutents selected from halo, cyano, hydroxy, NR$^v$R$^w$, or (1-3C)alkoxy, wherein R$^v$ and R$^w$ are each independently selected from hydrogen or (1-3C)alkyl;

(80) $A_5$ is selected from N or $CR^5$, where $R_5$ is selected from hydrogen, halo, cyano, hydroxy, NR$^q$R$^u$, (1-3C)alkyl, or (1-3C)alkoxy; wherein R$^q$ and R$^u$ are each independently selected from hydrogen or (1-3C)alkyl; and wherein any (1-3C)alkyl, (1-3C)alkoxy group present in a $R_5$ substituent group is optionally substituted by one or more substitutents selected from halo, cyano, hydroxy, NR$^v$R$^w$, or (1-2C)alkoxy, wherein R$^v$ and R$^w$ are each independently selected from hydrogen or (1-2C)alkyl;

(81) $A_5$ is CH;

(82) Ring A is:
a fused 5 or 6 membered heteroaryl ring comprising one or two heteroatoms independently from N, S or O; or
a fused 5, 6 or 7-membered heterocyclic ring comprising one or two heteroatoms independently from N, S or O;

(83) $A_6$ is selected from N, O, S, S(O)$_2$, $CR_6$, $C(R_6)_2$, $NR_{60}$, where $R_6$ is selected from hydrogen, oxo, fluoro, chloro, (1-2C)alkyl, (1-2C)alkoxy, (1-2C)haloalkoxy or (1-2C)haloalkyl; and
$R_{60}$ is hydrogen, O$^-$, (1-6C)alkyl, —C(O)—R$_{61}$, —C(O)O—R$_{61}$, or —C(O)N(R$_{62}$)R$_{61}$, wherein R$_{61}$ is selected from hydrogen, (1-6C)alkyl, aryl, 5 or 6 membered heteroaryl or 5 or 6 membered heterocyclyl and R$_{62}$ is selected from hydrogen or (1-2C)alkyl;

(84) $A_6$ is selected from N, O, S, S(O)$_2$, $CR_6$, $C(R_6)_2$, $NR_{60}$, where $R_6$ is selected from hydrogen, oxo, (1-2C)alkyl, (1-2C)alkoxy, (1-2C)haloalkoxy or (1-2C)haloalkyl; and
$R_{60}$ is hydrogen, O$^-$, (1-6C)alkyl, —C(O)—R$_{61}$, —C(O)O—R$_{61}$, or —C(O)N(R$_{62}$)R$_{61}$, wherein R$_{61}$ is selected from hydrogen or (1-6C)alkyl, and R$_{62}$ is selected from hydrogen or (1-2C)alkyl;

(85) $A_6$ is N;
(86) $A_7$ is selected from N, O, $CR_7$, S, $S(O)_2$, $C(R_7)_2$, $NR_{70}$, where $R_{70}$ is hydrogen, $O^-$, (1-6C)alkyl, —C(O)—$R_{71}$, —C(O)O—$R_{71}$, or —C(O)N($R_{72}$)$R_{71}$, wherein $R_{71}$ is selected from hydrogen, (1-6C)alkyl, aryl, 5 or 6 membered heteroaryl or 5 or 6 membered heterocyclyl and $R_{72}$ is selected from hydrogen or (1-2C)alkyl;
(87) $A_7$ is selected from N, O, $CR_7$, S, $S(O)_2$, $C(R_7)_2$, $NR_{70}$, where $R_{70}$ is hydrogen, $O^-$, (1-6C)alkyl, —C(O)—$R_{71}$, —C(O)O—$R_{71}$, or —C(O)N($R_{72}$)$R_{71}$, wherein $R_{71}$ is selected from hydrogen, (1-6C)alkyl, aryl, 5 or 6 membered heteroaryl or 5 or 6 membered heterocyclyl and $R_{72}$ is selected from hydrogen or (1-2C)alkyl;
(88) $A_7$ is $CR_7$;
(89) $R_7$ is selected from halo, cyano, oxo, or a group

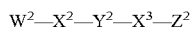
$W^2$—$X^2$—$Y^2$—$X^3$—$Z^2$ wherein
$W^2$ is absent or a linker group of the formula —[$CR^xR^y$]$_r$— in which r is an integer selected from 1, 2, or 3, and $R^x$ and $R^y$ are each independently selected from hydrogen or (1-2C)alkyl;
$X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —$SO_2$—, —$S(O)_2N(R^z)$—, or —$N(R^z)SO_2$, wherein $R^z$ is selected from hydrogen or methyl;
$Y^2$ is absent or a linker group of the formula —[$CR^{aa}R^{bb}$]$_s$— in which s is an integer selected from 1, 2, 3 or 4, and $R^{aa}$ and $R^{bb}$ are each independently selected from hydrogen or (1-2C)alkyl;
$X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —$SO_2$—, —$S(O)_2N(R^{cc})$—, or —$N(R^{cc})SO_2$, wherein $R^{cc}$ is selected from hydrogen or methyl; and
$Z^2$ is hydrogen, (1-6C)alkyl, (2-6C)alkenyl, aryl, (3-6C)cycloalkyl, heteroaryl, or heterocyclyl,
and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, $C(O)NR^{dd}R^{ee}$, $NR^{dd}C(O)R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;
and wherein any alkyl, aryl, heterocyclyl or heteroaryl group present in a substituent group on $Z^2$ is optionally further substituted by halo, cyano, nitro, hydroxy, caboxy, $NR^{ff}R^{gg}$, (1-2C)alkoxy, or (1-2C)alkyl; wherein $R^{ff}$ and $R^{gg}$ are selected from hydrogen or (1-2C)alkyl;
(90) $R_7$ is selected from halo, cyano, oxo, or a group

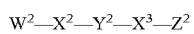
$W^2$—$X^2$—$Y^2$—$X^3$—$Z^2$ wherein
$W^2$ is absent or a linker group of the formula —[$CR^xR^y$]$_r$— in which r is an integer selected from 1, 2, or 3, and $R^x$ and $R^y$ are each independently selected from hydrogen or (1-2C)alkyl;
$X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —$SO_2$—, —$S(O)_2N(R^z)$—, or —$N(R^z)SO_2$, wherein $R^z$ is selected from hydrogen or methyl;
$Y^2$ is absent or a linker group of the formula —[$CR^{aa}R^{bb}$]$_s$— in which s is an integer selected from 1, 2, 3 or 4, and $R^{aa}$ and $R^{bb}$ are each independently selected from hydrogen or (1-2C)alkyl;
$X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —$SO_2$—, —$S(O)_2N(R^{cc})$—, or —$N(R^{cc})SO_2$, wherein $R^{cc}$ is selected from hydrogen or methyl; and
$Z^2$ is hydrogen, (1-6C)alkyl, (2-6C)alkenyl, phenyl, (3-6C)cycloalkyl, 5 or 6 membered heteroaryl, or 5 or 6 membered heterocyclyl,
and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, $C(O)NR^{dd}R^{ee}$, $NR^{dd}C(O)R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;
(91) m is 0 or 1;
(92) m is 0;
(93) m is 1;
(94) m is 2;
(95) $R_{11}$ is selected from halo, cyano, oxo, or a group

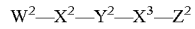
$W^2$—$X^2$—$Y^2$—$X^3$—$Z^2$ wherein
$W^2$ is absent or a linker group of the formula —[$CR^xR^y$]$_r$— in which r is an integer selected from 1, 2, or 3, and $R^x$ and $R^y$ are each independently selected from hydrogen or (1-2C)alkyl;
$X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —$SO_2$—, —$S(O)_2N(R^z)$—, or —$N(R^z)SO_2$, wherein $R^z$ is selected from hydrogen or methyl;
$Y^2$ is absent or a linker group of the formula —[$CR^{aa}R^{bb}$]$_s$— in which s is an integer selected from 1, 2, 3 or 4, and $R^{aa}$ and $R^{bb}$ are each independently selected from hydrogen or (1-2C)alkyl;
$X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —$SO_2$—, —$S(O)_2N(R^{cc})$—, or —$N(R^{cc})SO_2$, wherein $R^{cc}$ is selected from hydrogen or methyl; and
$Z^2$ is hydrogen, (1-6C)alkyl, (2-6C)alkenyl, aryl, (3-6C)cycloalkyl, heteroaryl, or heterocyclyl,
and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, $C(O)NR^{dd}R^{ee}$, $NR^{dd}C(O)R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;

and wherein any alkyl, aryl, heterocyclyl or heteroaryl group present in a substituent group on $Z^2$ is optionally further substituted by halo, cyano, nitro, hydroxy, caboxy, $NR^{ff}R^{gg}$, (1-2C)alkoxy, or (1-2C)alkyl; wherein $R^{ff}$ and $R^{gg}$ are selected from hydrogen or (1-2C)alkyl;

(96) $R_{11}$ is selected from halo, cyano, oxo, or a group $W^2—X^2—Y^2—X^3—Z^2$ wherein
- $W^2$ is absent or a linker group of the formula —$[CR^xR^y]_r$— in which r is an integer selected from 1, 2, or 3, and $R^x$ and $R^y$ are each independently selected from hydrogen or (1-2C)alkyl;
- $X^2$ is absent, —O—, —C(O)—, —C(O)O—, —OC(O)—, —N($R^z$)—, —N($R^z$)—C(O)—, —N($R^z$)—C(O)O—, —C(O)—N($R^z$)—, —S—, —SO—, —$SO_2$—, —S(O)$_2$N($R^z$)—, or —N($R^z$)SO$_2$, wherein $R^z$ is selected from hydrogen or methyl;
- $Y^2$ is absent or a linker group of the formula —$[CR^{aa}R^{bb}]_s$— in which s is an integer selected from 1, 2, 3 or 4, and $R^{aa}$ and $R^{bb}$ are each independently selected from hydrogen or (1-2C)alkyl;
- $X^3$ is absent, —O—, —C(O)—, —C(O)O—, —OC(O)—, —N($R^{cc}$)—, —N($R^{cc}$)—C(O)—, —N($R^{cc}$)—C(O)O—, —C(O)—N($R^{cc}$)—, —S—, —SO—, —$SO_2$—, —S(O)$_2$N($R^{cc}$)—, or —N($R^{cc}$)SO$_2$, wherein $R^{cc}$ is selected from hydrogen or methyl; and
- $Z^2$ is hydrogen, (1-6C)alkyl, (2-6C)alkenyl, phenyl, (3-6C)cycloalkyl, 5 or 6 membered heteroaryl, or 5 or 6 membered heterocyclyl,
  and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (1-2C)alkanoyl, (1-2C)alkylsulphonyl, C(O)$NR^{dd}R^{ee}$, $NR^{dd}$C(O)$R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl; or $R^{dd}$ and $R^{ee}$ can be linked such that, together with the nitrogen atom to which they are attached, they form a 4-6 membered heterocyclic ring;

(97) Q is a group of formula III as defined herein;

(98) Q is a group of formula III as defined herein in which Ring A is a fused 5 or 6-membered heterocyclic or ring comprising one N atom;

(99) Q is a group of formula:

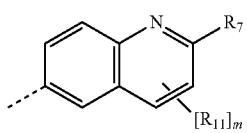

wherein $R_7$, $R_{11}$ and m each have any one of the definitions set out herein.

(100) Q is a group of formula:

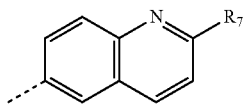

wherein $R_7$ has any one of the definitions set out herein.

(101) Q is a group of formula:

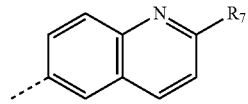

wherein $R_7$ is a group $W^2—X^2—Y^2—X^3—Z^2$ wherein
- $W^2$ is a linker group of the formula —$[CR^xR^y]_r$— in which r is 1, $R^x$ is hydrogen and $R^y$ is selected from hydrogen or methyl;
- $X^2$ is absent;
- $Y^2$ is absent;
- $X^3$ is absent; and
- $Z^2$ is a 4, 5, 6 or 7-membered nitrogen-linked heterocyclyl optionally comprising one further nitrogen atom,
  and wherein $Z^2$ is optionally further substituted by one or more substituent groups independently selected from oxo, halo, cyano, hydroxy, caboxy, $NR^{dd}R^{ee}$, (1-4C)alkoxy, (1-4C)alkyl, (3-6C)cycloalkyl, (3-6C)cycloalkyl(1-2C)alkyl, (2C)alkanoyl, (1-2C)alkylsulphonyl, C(O)$NR^{dd}R^{ee}$, $NR^{dd}$C(O)$R^{ee}$, $NR^{dd}SO_2R^{ee}$ and $SO_2NR^{dd}R^{ee}$; wherein $R^{dd}$ and $R^{ee}$ are each independently selected from hydrogen, (1-4C)alkyl, (3-6C)cycloalkyl;

(102) Q is a group of formula:

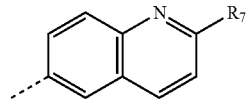

wherein $R_7$ is a group $W^2—X^2—Y^2—X^3—Z^2$ wherein
- $W^2$ is a linker group of the formula —$[CR^xR^y]_r$— in which r is 1, $R^x$ is hydrogen and $R^y$ is selected from hydrogen or methyl;
- $X^2$ is absent;
- $Y^2$ is absent;
- $X^3$ is absent; and
- $Z^2$ is a 4, 5, 6 or 7-membered nitrogen-linked heterocyclyl optionally comprising one further nitrogen atom,
  and wherein $Z^2$ is optionally further substituted on the further nitrogen atom by methyl, ethyl, propyl or cyclopropylmethyl and/or on a carbon atom by methyl, fluoro or chloro.

(103) Q is a group selected from:

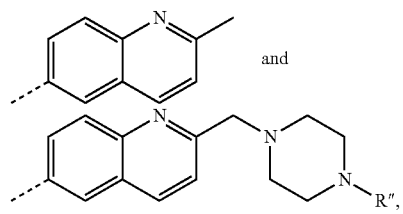

wherein R" is defined as hydrogen or (1-6C)alkyl; preferably R" is selected from hydrogen, methyl and ethyl, more preferably ethyl.

Suitably, R is as defined in any one of paragraphs (1) to (6) above. In an embodiment, R is as defined in any one of paragraphs (3) to (6) above. In a further embodiment, R is as defined in paragraph (5) or (6) above.

Suitably, $C_1$ is as defined in any one of paragraphs (7) to (11) above. In an embodiment, $C_1$ is as defined in any one of paragraphs (9) to (11) above. In a further embodiment, C, is as defined in paragraphs (10) or (11) above.

Suitably, $C_2$ is as defined in any one of paragraphs (12) to (16) above. In an embodiment, $C_2$ is as defined in any one of paragraphs (14) to (16) above. In a further embodiment, $C_2$ is as defined in paragraphs (15) or (16) above.

Suitably, both C, and $C_2$ are CH.

Suitably, $C_3$ is as defined in paragraphs (17) or (18) above.

Suitably, $C_4$ is as defined in paragraphs (19) or (20) above.

Suitably, a is 0 or 1.

Suitably, $R_b$ is methyl.

Suitably, when $C_3$ and $C_4$ are both O, a is 1 and $R_b$ is methyl.

In an embodiment, one of $C_3$ and $C_4$ is O and the other is CH. In an embodiment, one of $C_3$ and $C_4$ is O and the other is CH, a is 0 or 1 and $R_b$ is methyl.

Suitably, $C_5$ is as defined in any one of paragraphs (26) to (30) above. In an embodiment, $C_5$ is as defined in any one of paragraphs (28) to (30) above. In a further embodiment, $C_5$ is as defined in paragraphs (29) or (30) above.

Suitably, $C_6$ is as defined in any one of paragraphs (31) to (35) above. In an embodiment, $C_6$ is as defined in any one of paragraphs (33) to (35) above. In a further embodiment, $C_2$ is as defined in paragraphs (34) or (35) above.

Suitably, both $C_5$ and $C_6$ are CH.

Suitably, $C_7$ is as defined in paragraphs (36) or (37) above.

Suitably, $C_8$ is as defined in paragraphs (38) or (39) above.

Suitably, b is 0 or 1.

Suitably, $R_c$ is methyl.

Suitably, when $C_7$ and $C_8$ are both O, b is 1 and $R_c$ is methyl.

In an embodiment, one of $C_7$ and $C_8$ is O and the other is CH. In an embodiment, one of $C_7$ and $C_8$ is O and the other is CH, b is 0 or 1 and $R_b$ is methyl.

Suitably, $C_9$ is as defined in any one of paragraphs (44) to (48) above. In an embodiment, $C_5$ is as defined in any one of paragraphs (46) to (48) above. In a further embodiment, $C_5$ is as defined in paragraph (48) above.

Suitably, $C_{10}$ is as defined in any one of paragraphs (49) to (53) above. In an embodiment, $C_{10}$ is as defined in any one of paragraphs (51) to (53) above. In a further embodiment, $C_{10}$ is as defined in paragraph (53) above.

Suitably, both $C_9$ and $C_{10}$ are CH.

Suitably, $C_{11}$ is as defined in paragraphs (54) or (55) above, especially paragraph (54).

Suitably, $C_{12}$ is as defined in paragraphs (56) or (57) above, especially paragraph (56).

Suitably, c is 0 or 1, especially 0.

Suitably, $R_d$ is methyl.

Suitably, $C_7$ and $C_8$ are both O.

Suitably, in compounds of formula I $R_4$ has any one of the definitions set out in paragraphs (64) to (67) above. Most suitably, $R_4$ is as defined in any one of paragraphs (65), (66) or (67) above. In a particular embodiment, $R_4$ is as defined in paragraph (67) above.

Suitably, in compounds of formula I, Q is as defined in any one of paragraphs (68), (69) or (97) to (103) above.

In an embodiment of the compounds of formula I, Q has one of the structural formulae IIa, IIb, IIc, IId, IIe, IIIa and IIIb shown below:

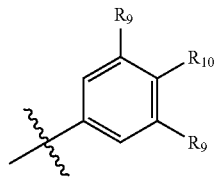
IIa

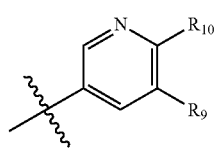
IIb

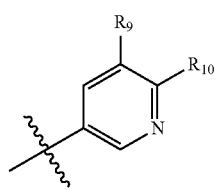
IIc

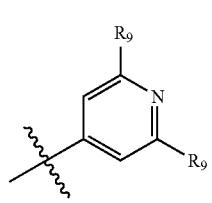
IId

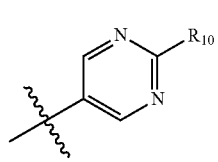
IIe

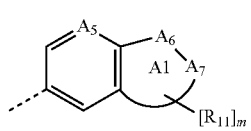
IIIa

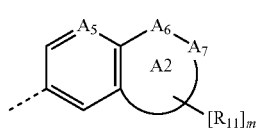
IIIb wherein $R_9$, $R_{10}$, $A_5$, $A_6$, $A_7$, $R_{11}$ and m each have any one of the definitions hereinbefore;

ring A1 is a fused 5-membered carbocyclic ring, 5-membered heterocyclic ring or 5-membered heteroaryl ring;

ring A2 is a fused 6 or 7-membered carbocyclic ring, 6 or 7-membered heterocyclic ring or 6-membered heteroaryl ring.

Suitably, in compounds of formula I, ring A1 is a fused 5-membered heterocyclic ring or 5-membered heteroaryl ring comparing one or two heteroatoms selected from N, O or S.

Suitably, in compounds of formula I, ring A2 is a fused 6-membered heterocyclic or 6-membered heteroaryl comparing one or two heteroatoms selected from N, O or S.

In an embodiment of the compounds of formula I, Q is a group of structural formula IIIa or IIIb as shown above.

In a particular embodiment of the compounds of formula I, Q is a group of structural formula IIIb as defined above.
In an embodiment of the compounds of formula I, Q is selected from one of the following:
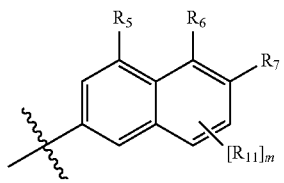
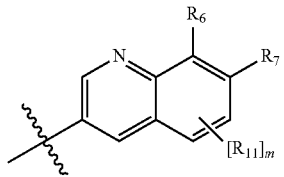
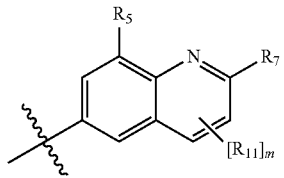
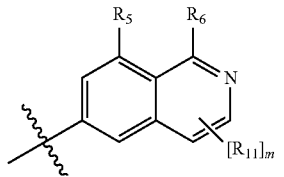
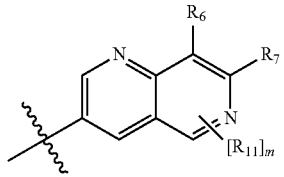
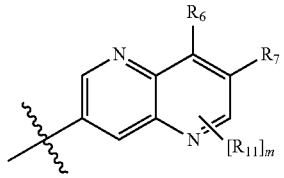
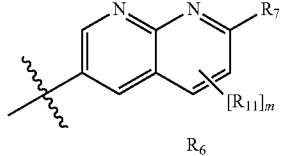
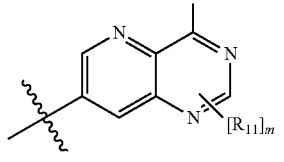
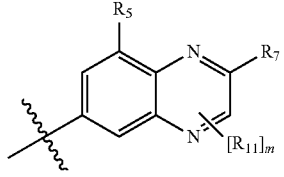
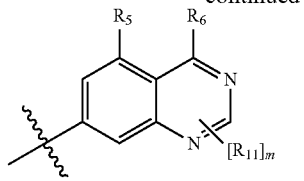
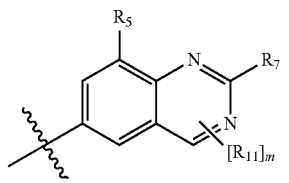
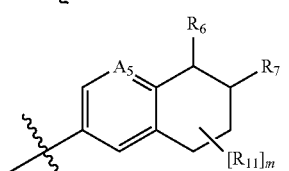
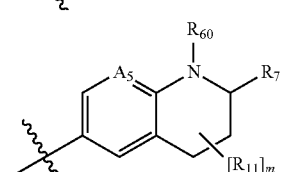
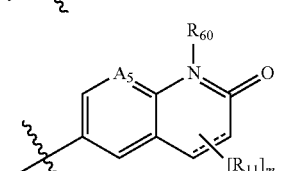
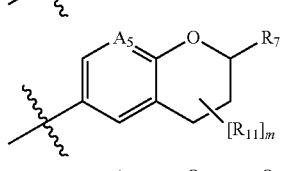
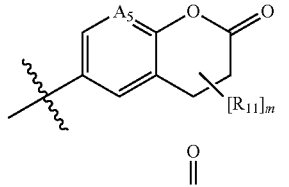
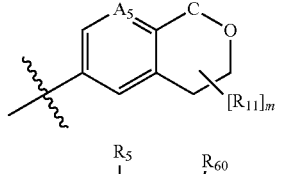
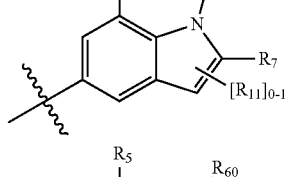

-continued
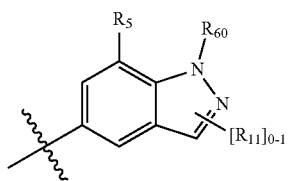
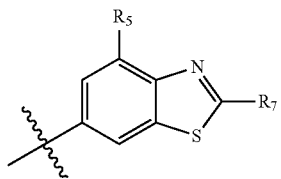
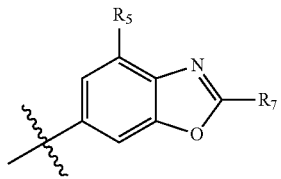
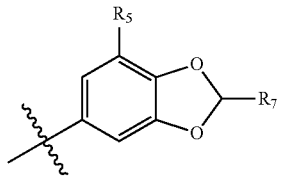
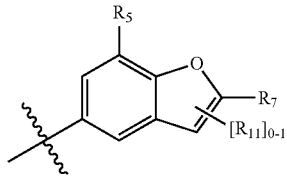
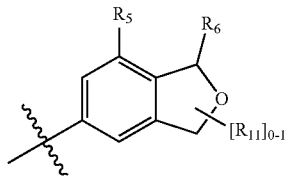
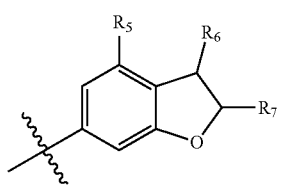
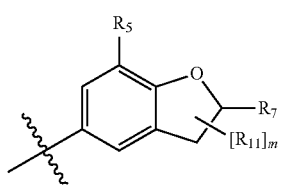
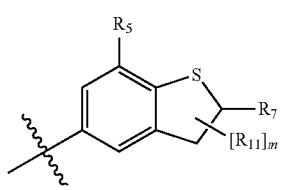
-continued
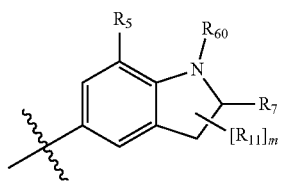
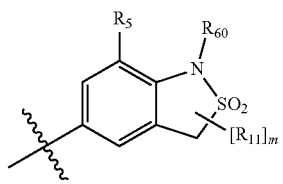
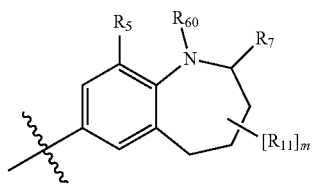
wherein $A_5$, $R_5$, $R_6$, $R_7$, $R_{60}$, $R_{11}$ and m each have any one of the definitions herein.
In an embodiment of the compounds of formula I, Q is selected from:
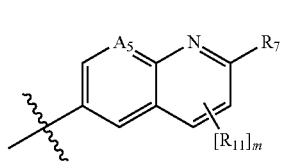
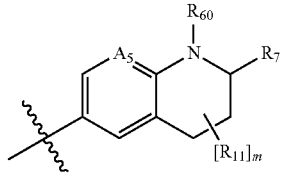
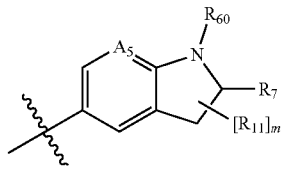
wherein $A_5$, $R_{60}$, $R_7$, $R_{11}$ and m each have any one of the definitions herein.
In an embodiment of the compounds of formula I, Q is selected from:
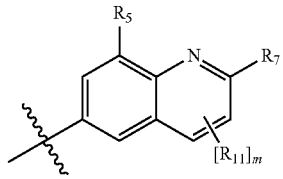

-continued

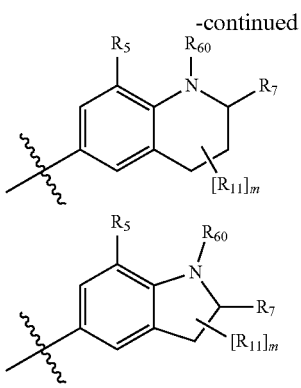

wherein $R_5$, $R_{60}$, $R_7$, $R_{11}$ and m each have any one of the definitions herein.

In a particular embodiment of the compounds of formula I, Q is selected from:

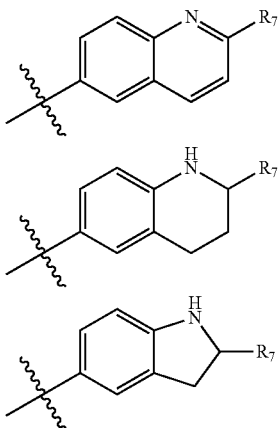

wherein $R_7$ has any one of the definitions set out hereinbefore.

In a particular embodiment of the compounds of formula I, Q is:

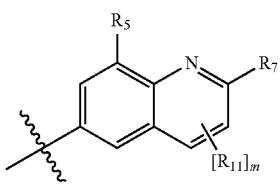

wherein $R_5$, $R_7$, $R_{11}$ and m each have any one of the definitions herein.

In a particular embodiment of the compounds of formula I, Q is:

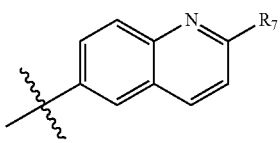

wherein $R_7$ has any one of the definitions set out hereinbefore.

Suitably, $R_7$ is as defined in any one of paragraphs (89) or (90) above.

In another embodiment of the invention, the compounds of the invention are of formula (V):

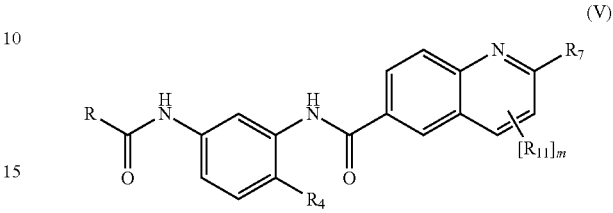

(V)

wherein R, $R_4$, $R_7$, $R_{11}$ and m are defined above, with the proviso that when $R_4$ and $R_7$ are methyl, and m is 0 then R is not

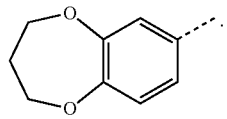

Suitably, in compounds of formula V, R is as defined in any one of paragraphs (1) to (6) above. In one embodiment, R is as defined in any one of paragraphs (3) to (6) above. In a further embodiment, R is as defined in paragraph (5) or (6) above.

Suitably, in compounds of formula V, R is selected from the group consisting of:

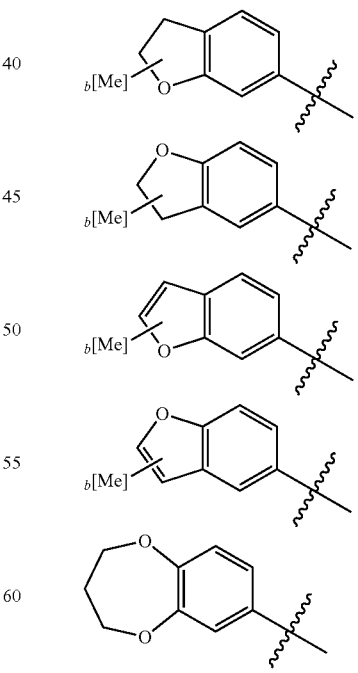

wherein a and b can independently be 0 or 1.

Suitably, in compounds of formula V, R is selected from the group consisting of:

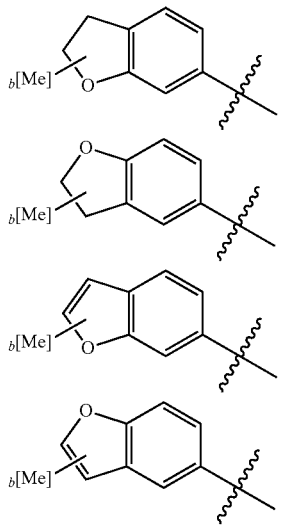

wherein a and b can independently be 0 or 1.

Suitably, in compounds of formula V, $R_4$ has any one of the definitions set out in paragraphs (64) to (67) above. Most suitably, $R_4$ is as defined in any one of paragraphs (65), (66) or (67) above. In one embodiment, $R_4$ is as defined in paragraph (67) above. In another embodiment, $R_4$ is methyl or fluoro.

Suitably, in compounds of formula V, $R_7$ is as defined in any one of paragraphs (89) or (90) above. In a particular embodiment, $R_7$ is methyl or (4-ethylpiperazin-1-yl)methyl.

Suitably, in compounds of formula V, $R_{11}$ is as defined in any one of paragraphs (95) or (96) above.

Suitably, in compounds of formula V, m is 0, 1 or 2. In one embodiment, m is 0.

In another embodiment of the invention, the compounds of the invention are of formula (VI):

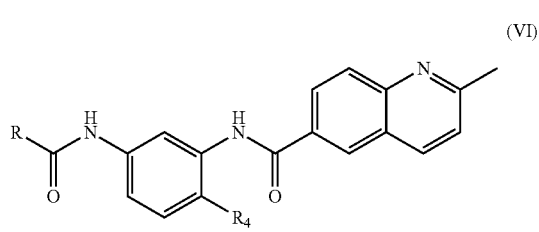

(VI)

wherein R and $R_4$ are defined above, with the proviso that when $R_4$ is methyl then R is not

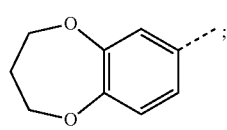

Suitably, in compounds of formula VI, R is as defined in any one of paragraphs (1) to (6) above. In one embodiment, R is as defined in any one of paragraphs (3) to (6) above. In a further embodiment, R is as defined in paragraph (5) or (6) above.

Suitably, in compounds of formula VI, R is selected from the group consisting of:

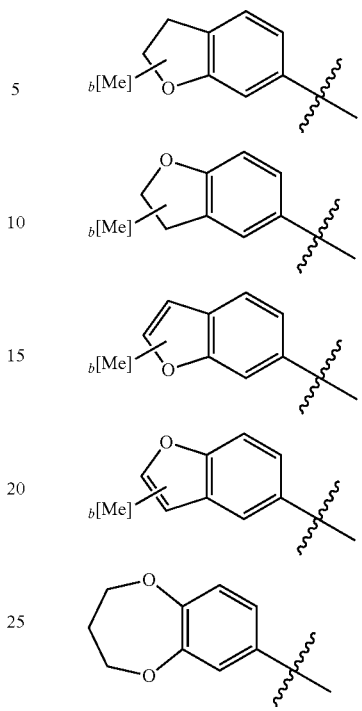

wherein a and b can independently be 0 or 1.

Suitably, in compounds of formula VI, R is selected from the group consisting of:

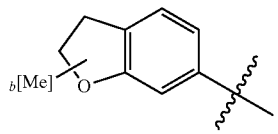

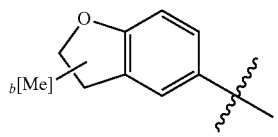

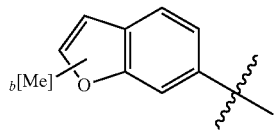

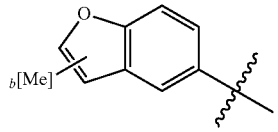

wherein a and b can independently be 0 or 1.

Suitably, in compounds of formula VI, $R_4$ has any one of the definitions set out in paragraphs (64) to (67) above. Most suitably, $R_4$ is as defined in any one of paragraphs (65), (66) or (67) above. In one embodiment, $R_4$ is as defined in paragraph (67) above. In another embodiment, $R_4$ is methyl or fluoro.

In another embodiment of the invention, the compounds of the invention are of formula (VII):

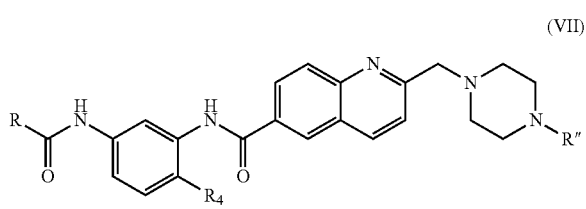

(VII)

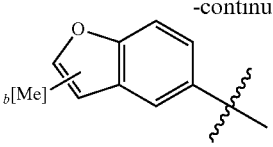

-continued wherein a and b can independently be 0 or 1.

Suitably, in compounds of formula VII, $R_4$ has any one of the definitions set out in paragraphs (64) to (67) above. Most suitably, $R_4$ is as defined in any one of paragraphs (65), (66) or (67) above. In one embodiment, $R_4$ is as defined in paragraph (67) above. In another embodiment, $R_4$ is methyl or fluoro.

Suitably, in compounds of formula VII, R" is selected from hydrogen, methyl or ethyl, preferably ethyl.

In another embodiment of the invention, the compounds of the invention are of formula (VIII):

wherein R and $R_4$ are defined above, and R" is selected from hydrogen and (1-6C)alkyl.

Suitably, in compounds of formula VII, R is as defined in any one of paragraphs (1) to (6) above. In one embodiment, R is as defined in any one of paragraphs (3) to (6) above. In a further embodiment, R is as defined in paragraph (5) or (6) above.

Suitably, in compounds of formula VII, R is selected from the group consisting of:

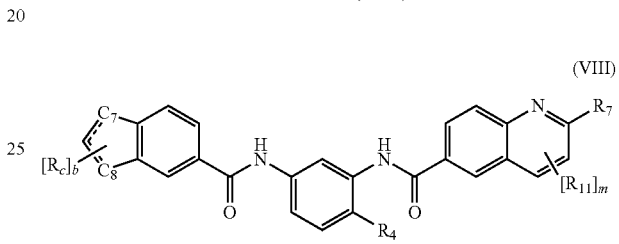

(VIII)

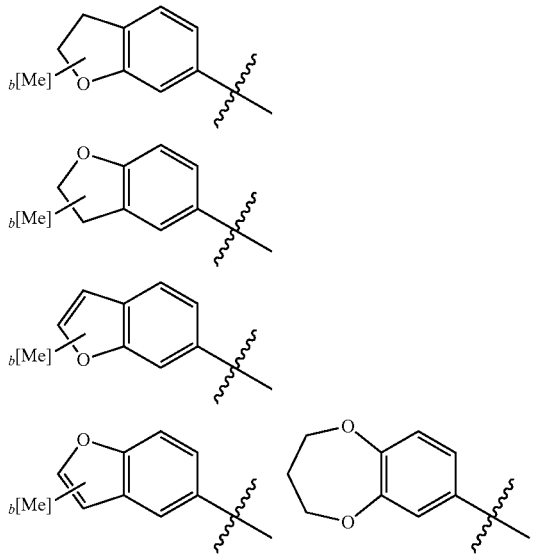

wherein $R_4$, $R_7$, $R_{11}$, m, $R_c$, b, $C_7$ and $C_8$ are defined above.

Suitably, in compounds of formula VIII, $R_4$ has any one of the definitions set out in paragraphs (64) to (67) above. Most suitably, $R_4$ is as defined in any one of paragraphs (65), (66) or (67) above. In one embodiment, $R_4$ is as defined in paragraph (67) above. In one embodiment, $R_4$ is as defined in paragraph (67) above. In another embodiment, $R_4$ is methyl or fluoro.

Suitably, in compounds of formula VIII, $R_7$ is as defined in any one of paragraphs (89) or (90) above. In a particular embodiment, $R_7$ is methyl.

Suitably, in compounds of formula VIII, $R_{11}$ is as defined in any one of paragraphs (95) or (96) above.

Suitably, in compounds of formula VIII, m is 0, 1 or 2. In a particular embodiment, m is 0.

Suitably, in compounds of formula VIII, $C_7$ is as defined in paragraphs (36) and (37) above.

Suitably, in compounds of formula VIII, $C_8$ is as defined in paragraphs (38) and (39) above.

Suitably, in compounds of formula VIII, b is 0 or 1.

Suitably, in compounds of formula VIII, $R_c$ is methyl.

Suitably, when $C_7$ and $C_8$ are both O, b is 1 and $R_c$ is methyl.

In an embodiment, one of $C_7$ and $C_8$ is O and the other is CH. In an embodiment, one of $C_7$ and $C_8$ is O and the other is CH, b is 0 or 1 and $R_b$ is methyl.

Particular compounds of the present invention include any one of the compounds exemplified in the present application, or a pharmaceutically acceptable salt or solvate thereof, and, in particular, any one of the following:

N-(5-(2,3-dihydrobenzofuran-6-carboxamido)-2-methylphenyl)-2-methylquinoline-6-carboxamide;

N-(5-(2,3-dihydrobenzofuran-5-carboxamido)-2-methylphenyl)-2-methylquinoline-6-carboxamide;

N-(5-(2,3-dihydrobenzofuran-6-carboxamido)-2-fluorophenyl)-2-((4-ethylpiperazin-1-yl)methyl)quinoline-6-carboxamide;

wherein a and b can independently be 0 or 1.

Suitably, in compounds of formula VII, R is selected from the group consisting of:

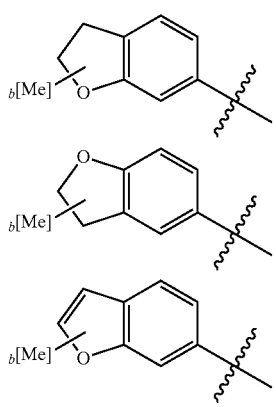

N-(5-(benzofuran-6-carboxamido)-2-methylphenyl)-2-methylquinoline-6-carboxamide;
N-(2-chloro-5-(2,3-dihydrobenzofuran-6-carboxamido)phenyl)-2-((4-ethylpiperazin-1-yl)methyl)quinoline-6-carboxamide;
N-(5-(2,3-dihydrobenzofuran-6-carboxamido)-2-methylphenyl)-2-((4-ethylpiperazin-1-yl)methyl)quinoline-6-carboxamide;
N-(5-(chroman-7-carboxamido)-2-methylphenyl)-2-methylquinoline-6-carboxamide;
N-(5-(chroman-7-carboxamido)-2-fluorophenyl)-2-methylquinoline-6-carboxamide;
N-(5-(chroman-7-carboxamido)-2-fluorophenyl)-2-((4-ethylpiperazin-1-yl)methyl)quinoline-6-carboxamide;
N-(5-(2,3-dihydrobenzofuran-6-carboxamido)-2-fluorophenyl)-2-methylquinoline-6-carboxamide;
N-(2-chloro-5-(2,3-dihydrobenzofuran-6-carboxamido)phenyl)-2-methylquinoline-6-carboxamide;
rac-2-methyl-N-(2-methyl-5-(2-methyl-2,3-dihydrobenzofuran-5-carboxamido)phenyl)quinoline-6-carboxamide;
N-(2-chloro-5-(chroman-7-carboxamido)phenyl)-2-methylquinoline-6-carboxamide;
2-(azetidin-1-ylmethyl)-N-(2-chloro-5-(2,3-dihydrobenzofuran-6-carboxamido)phenyl)quinoline-6-carboxamide;
2-(azetidin-1-ylmethyl)-N-(5-(2,3-dihydrobenzofuran-6-carboxamido)-2-fluorophenyl)quinoline-6-carboxamide;
(rac)-2-methyl-N-(2-methyl-5-(2-methyl-2,3-dihydrobenzofuran-6-carboxamido)phenyl)quinoline-6-carboxamide;
N-(5-(benzo[d][1,3]dioxole-5-carboxamido)-2-methylphenyl)-2-methylquinoline-6-carboxamide;
2-(azetidin-1-ylmethyl)-N-(2-chloro-5-(chroman-7-carboxamido)phenyl)quinoline-6-carboxamide;
rac-2-methyl-N-(2-methyl-5-(3-methyl-2,3-dihydrobenzo[b][1,4]dioxine-6-carboxamido)phenyl)quinoline-6-carboxamide;
rac-N-(2-fluoro-5-(3-methyl-2,3-dihydrobenzo[b][1,4]dioxine-6-carboxamido)phenyl)-2-methylquinoline-6-carboxamide;
N-(5-(3,4-dihydro-2H-benzo[b][1,4]dioxepine-7-carboxamido)-2-methylphenyl)-2-methylquinoline-6-carboxamide;
or a pharmaceutically acceptable salt or solvate thereof.
Further compounds of the invention include any one of the following:
2-((4-ethylpiperazin-1-yl)methyl)-N-(2-fluoro-5-(3-methyl-2,3-dihydrobenzo[b][1,4]dioxine-6-carboxamido)phenyl)quinoline-6-carboxamide;
N-(2-chloro-5-(3-methyl-2,3-dihydrobenzo[b][1,4]dioxine-6-carboxamido)phenyl)-2-((4-ethylpiperazin-1-yl)methyl)quinoline-6-carboxamide
2-(azetidin-1-ylmethyl)-N-(2-chloro-5-(3-methyl-2,3-dihydrobenzo[b][1,4]dioxine-6-carboxamido)phenyl)quinoline-6-carboxamide;
2-(azetidin-1-ylmethyl)-N-(2-fluoro-5-(3-methyl-2,3-dihydrobenzo[b][1,4]dioxine-6-carboxamido)phenyl)quinoline-6-carboxamide;
2-methyl-N-(5-(3-methyl-2,3-dihydrobenzo[b][1,4]dioxine-6-carboxamido)-2-(3-(pyrrolidin-1-yl)propyl)phenyl)quinoline-6-carboxamide;
N-(3-(4-fluorobenzamido)-4-(3-(pyrrolidin-1-yl)propyl)phenyl)-3-methyl-2,3-dihydrobenzo[b][1,4]dioxine-6-carboxamide;
N-(5-(3,4-dihydro-2H-benzo[b][1,4]dioxepine-7-carboxamido)-2-fluorophenyl)-2-((4-ethylpiperazin-1-yl)methyl)quinoline-6-carboxamide;
N-(2-chloro-5-(3,4-dihydro-2H-benzo[b][1,4]dioxepine-7-carboxamido)phenyl)-2-((4-ethylpiperazin-1-yl)methyl)quinoline-6-carboxamide
2-(azetidin-1-ylmethyl)-N-(2-chloro-5-(3,4-dihydro-2H-benzo[b][1,4]dioxepine-7-carboxamido)phenyl)quinoline-6-carboxamide
2-(azetidin-1-ylmethyl)-N-(5-(3,4-dihydro-2H-benzo[b][1,4]dioxepine-7-carboxamido)-2-fluorophenyl)quinoline-6-carboxamide;
N-(5-(3,4-dihydro-2H-benzo[b][1,4]dioxepine-7-carboxamido)-2-(3-(pyrrolidin-1-yl)propyl)phenyl)-2-methylquinoline-6-carboxamide;
N-(3-(4-fluorobenzamido)-4-(3-(pyrrolidin-1-yl)propyl)phenyl)-3,4-dihydro-2H-benzo[b][1,4]dioxepine-7-carboxamide;
N-(5-(2,3-dihydrobenzofuran-6-carboxamido)-2-(3-(pyrrolidin-1-yl)propyl)phenyl)-2-methylquinoline-6-carboxamide;
N-(3-(4-fluorobenzamido)-4-(3-(pyrrolidin-1-yl)propyl)phenyl)-2,3-dihydrobenzofuran-6-carboxamide;
2-methyl-N-(5-(2-methyl-2,3-dihydrobenzofuran-6-carboxamido)-2-(3-(pyrrolidin-1-yl)propyl)phenyl)quinoline-6-carboxamide;
N-(3-(4-fluorobenzamido)-4-(3-(pyrrolidin-1-yl)propyl)phenyl)-2-methyl-2,3-dihydrobenzofuran-6-carboxamide;
N-(5-(chroman-7-carboxamido)-2-(3-(pyrrolidin-1-yl)propyl)phenyl)-2-methylquinoline-6-carboxamide;
N-(3-(4-fluorobenzamido)-4-(3-(pyrrolidin-1-yl)propyl)phenyl)chroman-7-carboxamide.
or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess HSF1 pathway inhibitory activity.

The present invention also encompasses compounds of the invention as defined herein which comprise one or more isotopic substitutions. For example, H may be in any isotopic form, including $^1H$, $^2H$ (D) and $^3H$ (T); C may be in any isotopic form including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess HSF1 pathway inhibitory activity.

It is also to be understood that certain compounds of the invention may exhibit polymorphism, and that the invention encompasses all such forms that possess HSF1 pathway inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

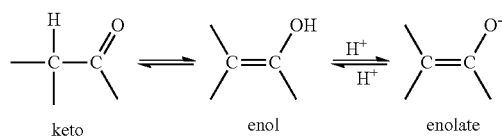

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I or IA as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I or IA is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$ amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described herein, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The compounds of the invention may be prepared using synthetic techniques that are known in the art (as illustrated in the accompanying examples).

In a particular aspect, the present invention provides a method of synthesising a compound of the formula I as defined herein, or a pharmaceutically acceptable salt or solvate thereof, the method comprising:
a) reacting a compound of formula A:

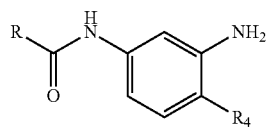

Formula A wherein R and $R_4$ each have any one of the meanings as defined hereinbefore;
with a compound of formula B:

Q-COOH          Formula B wherein Q is as defined herein; and
b) optionally thereafter, and if necessary:
  i) removing any protecting groups present;
  ii) converting the compound formula I into another compound of formula I; and/or
  iii) forming a pharmaceutically acceptable salt or solvate thereof.

Suitably the coupling reaction between formula A and formula B takes place in the presence of a suitable solvent. Any suitable solvent or solvent mixture may be used for this reaction. A person skilled in the art will know how to select suitable solvents or solvent mixtures for use in these reactions. Examples of suitable solvents include DMA, 1,4-dioxane, DMF and toluene.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out at room temperature or at an elevated temperature for a suitable time period of, for example, 2 hours to 7 days, or more suitably 2 to 10 hours. If desired, the reaction mixture may be heated either conventionally or by using microwave irradiation.

Suitably the coupling reaction between formula A and formula B takes place in the presence of a coupling agent. Suitable coupling agents are known in the art and described in, for example, Chem. Soc. Rev., 2009, 38, 606-631. An example of a suitable coupling agent is HATU.

The compound of formula A can be prepared by processes known in the art, and suitably by the processes described herein with reference to the examples.

The compound of formula B can be prepared by processes known in the art, and suitably by the processes described herein with reference to the examples.

In step (b) of the above processes, if a suitable protecting group is present then additional deprotection conditions may be employed. Suitable protecting groups include tert-butoxycarbonate and dimethylacetal. Typical conditions comprise a suitable acid in a suitable solvent such as trifluoroacetic acid in either DCM or THF.

A racemic compound of formula I may be separated using suitable chiral separation chromatography to furnish the desired enantiomers.

In another aspect, the present invention provides a method of synthesising a compound of the formula I, or a pharmaceutically acceptable salt or solvate thereof, the method comprising:
a) reacting a compound of formula C:

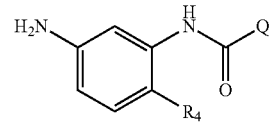

Formula C wherein Q and $R_4$ each have any one of the meanings as defined hereinbefore;
with a compound of formula D:

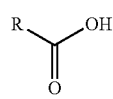

Formula D wherein R is as defined hereinbefore; and
b) optionally thereafter, and if necessary:
  i) removing any protecting groups present;
  ii) converting the compound formula II into another compound of formula II; and/or
  iii) forming a pharmaceutically acceptable salt or solvate thereof.

Suitably the reaction conditions for the coupling between compound C and compound D are as defined above for the coupling between compounds A and B.

In a further aspect of the invention, there is provided a compound of formula I obtainable by/obtained by/or directly obtained by any one of the processes defined or exemplified herein.

Biological Activity

The following biological assays may be used to measure the pharmacological effects of the compounds of the present invention.

Cell-Based ELISA (Cellisa) Assay

U2OS cells ($5-8 \times 10^4$ cells/mL) or SK-OV-3 cells ($5-8 \times 10^4$ cells/mL) were seeded into 96-well plates and incubated at 37° C. for 48 h. Compounds were then added at a range of concentrations and incubated for 1 h before addition of 17-AAG (250 nM). Cells were then incubated for 18 h. The medium was removed washed 2× with PBS and cells were then fixed with fixing solution (4% paraformaldehyde, 0.3% TritonX-100 in PBS) for 30 min at 4° C. The plates were then washed 2× with PBS before blocking with 5% milk for 30 min at 37° C. After washing the plates 4× with 0.1% Tween-20/deionised water, HSP72 antibody (SPA-810, Enzo Life) was added for 1.5 h at 37° C. Following 4× washes, the plates were incubated with europium-labelled anti-mouse antibody (0.6 ug/ml) in Delfia assay buffer (Perkin Elmer) for 1 h at 37° C. After washing the plates, Delfia enhancement solution was added, shaken for 10 min before reading in the Envision plate reader (Perkin-Elmer) with excitation at 340 nm and emission at 615 nm. The plates were washed again before protein determination using the bicinchoninic acid assay (BCA assay, Pierce Biotechnology). The europium counts were normalised for the amount of protein in each well. The 50% inhibitory concentration value of the compound was then calculated.

In general, activity possessed by compounds of the formula I, may be demonstrated in the Cellisa assay by an $IC_{50}$ value of less than 15 µM. Suitably compounds have an $IC_{50}$ value of less than 10 µM in these assays, more suitably less than 5 µM, even more suitably less than 2 µM and most suitably less than 1 µM. Preferred compounds of the invention have an $IC_{50}$ value of less than 500 nM in the Cellisa assay.

The activities of compounds of the invention in the above assay are shown in the accompanying example section.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the present invention function as inhibitors of HSF1 pathway activity. Accordingly, the compounds of the invention are potentially useful agents for the treatment of diseases or conditions in which HSF1 pathway activity is implicated.

In one aspect, the present invention provides a compound of formula I, or a pharmaceutically acceptable salt or solvate thereof, or a pharmaceutical composition as defined herein for use in therapy.

In another aspect, the present invention provides a method of inhibiting HSF1 pathway activity in a cell, the method comprising administering to said cell compound of formula I as defined herein, or a pharmaceutically acceptable salt or solvate thereof.

In a further aspect, the present invention provides a method of inhibiting HSF1 pathway in vitro or in vivo, said method comprising contacting a cell with an effective amount of a compound, or a pharmaceutically acceptable salt or solvate thereof, as defined herein.

In another aspect, the present invention provides a method of inhibiting HSF1 pathway activity in a human or animal subject in need of such inhibition, the method comprising administering to said subject an effective amount of a compound of formula I as defined herein, or a pharmaceutically acceptable salt or solvate thereof.

In another aspect, the present invention provides a compound of formula I as defined herein, or a pharmaceutically acceptable salt or solvate thereof for use in the treatment of disease or condition associated with HSF1 pathway activity.

In another aspect, the present invention provides the use of a compound of formula I as defined herein, or a pharmaceutically acceptable salt or solvate thereof, in the manufacture of a medicament for use in the treatment of disease or condition associated with HSF1 pathway activity.

In yet another aspect, the present invention provides a method of treating a proliferative disorder in a human or animal subject, the method comprising administering to said subject a therapeutically acceptable amount of a compound of formula I as defined herein, or a pharmaceutically acceptable salt or solvate thereof.

HSF1 pathway activity has been implicated in several diseases, including cancer, and autoimmune, and viral diseases.

The broad activity of HSF1 pathway and the role it plays in many disease states is discussed in the scientific literature, see for example:

Evans, C. G.; Chang, L.; Gestwicki, J. E., Heat Shock Protein 70 (Hsp70) as an Emerging Drug Target. *J Med Chem* 2010, 53 (12), 4585-4602;

Calderwood, S. K.; Khaleque, M. A.; Sawyer, D. B.; Ciocca, D. R., Heat shock proteins in cancer: chaperones of tumorigenesis. *Trends Biochem Sci* 2006, 31 (3), 164-172;

Dai, C.; Whitesell, L.; Rogers, A. B.; Lindquist, S., Heat shock factor 1 is a powerful multifaceted modifier of carcinogenesis. *Cell* 2007, 130 (6), 1005-1018;

Whitesell, L.; Lindquist, S., Inhibiting the transcription factor HSF1 as an anticancer strategy. *Expert Opin Ther Tar* 2009, 13 (4), 469-478; and Powers, M. V.; Workman, P., Inhibitors of the heat shock response: Biology and pharmacology. *Febs Lett* 2007, 581 (19), 3758-3769;

the entire contents of which are incorporated herein by reference.

HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g. promyelocytic leukemia), head and neck cancer, and Hodgkin's disease.

In yet another aspect, the present invention provides a compound of formula I as defined herein, or a pharmaceutically acceptable salt or solvate thereof, for use in the treatment of a proliferative disorder.

In yet another aspect, the present invention provides the use of a compound of formula I as defined herein, or a pharmaceutically acceptable salt or solvate thereof, in the manufacture of a medicament for use in the treatment of a proliferative disorder.

The term "proliferative disorder" are used interchangeably herein and pertain to an unwanted or uncontrolled cellular proliferation of excessive or abnormal cells which is undesired, such as, neoplastic or hyperplasticgrowth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their HSF1 pathway inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery, radiotherapy or therapy with a chemotherapeutic agent or a molecularly targeted agent. Such additional therapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; J. Med. Chem., 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) HSP90 inhibitors (for example, geldanamycin, radicicol or 17-N-Allylamino-17-demethoxygeldanamycin (17AAG));

(ix) antisense therapies, for example those which are directed to the targets listed above, such as ISIS 2503, an anti-ras antisense;

(x) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (xi) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

It is anticipated that the HSF1 pathway inhibitors of the present invention are particularly suited to combination therapy with anti-tumour agents that inhibit HSP90 (for example, geldanamycin, radicicol or 17-N-Allylamino-17-demethoxygeldanamycin (17AAG)).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(xi) above.

In a further aspect of the invention there is provided a compound of the invention or a pharmaceutically acceptable salt or solvate thereof, in combination with an anti-tumour agent selected from one listed under (i)-(xi) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(xi) herein above, in association with a pharmaceutically acceptable diluent or carrier.

In another aspect, the compounds of the present invention may be used for the treatment of other HSF1 pathway-mediated diseases or conditions, such as autoimmune and viral diseases. In the case of autoimmune diseases, the compounds of the invention may be combined with other agents for the treatment of autoimmune conditions, for example, steroids and other immunosupressent agents. In the case of viral diseases, the compounds of the invention may be administered with one or more additional antiviral agents.

EXAMPLES

Compound 1, 1-(Allyloxy)-3-bromobenzene

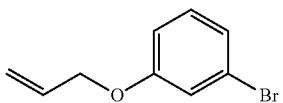

3-Bromophenol (6.21 g, 35.9 mmol) was dissolved in acetonitrile (45 ml) and K$_2$CO$_3$ (8.93 g, 64.6 mmol) and allyl bromide (3.42 ml, 39.5 mmol) added. The reaction heated at 80° C. for 1.5 hours after which the reaction was cooled to room temp and the resulting suspension filtered. The filtrate was concentrated under reduced pressure to give the title compound as a pale yellow oil (7.74 g, quant.). $^1$H NMR (500 MHz, CDCl$_3$) b 7.17-7.05 (m, 3H), 6.88-6.82 (m, 1H), 6.09-5.97 (m, 1H), 5.41 (app. dq, J=17.3, 1.6 Hz, 1H), 5.30 (app. dq, J=10.5, 1.4 Hz, 1H), 4.52 (dt, J=5.3, 1.6 Hz, 2H).

Compound 2, 2-Allyl-5-bromophenol

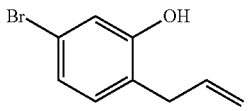

1-(Allyloxy)-3-bromobenzene (7.74 g, 36.3 mmol) was dissolved in N-methylaniline (8 ml) and the reaction heated in the microwave for 8 hours at 180° C. The reaction mixture was diluted with EtOAc and washed with 1M HCl. The organic layer was separated, dried over Na$_2$SO$_4$ and evaporated under reduced pressure to give the crude product as a brown oil. Purification via flash column chromatography on silica gel, gradient: cyclohexane/EtOAc from 5 to 10% gave the title compound as a colourless oil (1.14 g, 15%). $^1$H NMR (500 MHz, CDCl$_3$) δ 7.07-6.92 (m, 3H), 6.02-5.93 (m, 1H), 5.21-5.11 (m, 2H), 5.01 (s, 1H), 3.36 (dt, J=6.3, 1.6 Hz, 2H).

Compound 3, (rac)-6-Bromo-2-methyl-2,3-dihydrobenzofuran

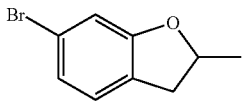

2-Allyl-5-bromophenol (1.14 g, 5.35 mmol) was dissolved in DCM (10 ml) and trifluoromethanesulfonic acid (24.0 µl, 0.268 mmol) added. The reaction was heated in the microwave for 1 hour at 100° C. The reaction mixture was diluted with 1M HCl and Et$_2$O. The organic layer was washed with 0.1M HCl, dried over Na$_2$SO$_4$ and evaporated to give the title compound as a yellow oil (0.916 g, 80%). $^1$H NMR (500 MHz, CDCl$_3$) b 7.02-6.87 (m, 3H), 5.00-4.89 (m, 1H), 3.25 (ddd, J=15.5, 9.0, 1.0 Hz, 1H), 2.74 (ddd, J=15.5, 7.5, 1.2 Hz, 1H), 1.45 (d, J=6.3 Hz, 3H).

Compound 4, (rac)-2-Methyl-2,3-dihydrobenzofuran-6-carboxylic acid

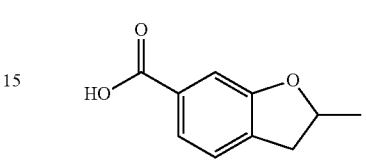

6-Bromo-2-methyl-2,3-dihydrobenzofuran (0.910 g, 4.27 mmol) was dissolved in THF (20 ml) and was cooled to −78° C. nBuLi (2.3 M in hexanes, 2.32 mL, 5.34 mmol) was added and the reaction stirred at −78° C. for 1 hour. Solid CO$_2$ was added and the reaction stirred at −78° C. for 10 mins before warming slowing to just below room temp. Once effervescence was complete the reaction was quenched by the addition of water and warmed to room temperature. The reaction mixture was diluted with EtOAc and water and the aqueous layer acidified to pH 2. The organic layer was separated, dried over Na$_2$SO$_4$ and evaporated under reduced pressure. The crude material was recrystallised from EtOAc and the crystals washed with cold Et$_2$O to give the title compound as a white crystalline solid (0.355 g, 47%). $^1$H NMR (500 MHz, CDCl$_3$) (7.62 (dd, J=7.7, 1.5 Hz, 1H), 7.43 (d, J=1.4 Hz, 1H), 7.22 (d, J=7.6 Hz, 1H), 5.05-4.94 (m, 1H), 3.37 (ddd, J=16.3, 8.8, 1.1 Hz, 1H), 2.86 (ddd, J=16.2, 7.6, 1.2 Hz, 1H), 1.48 (d, J=6.3 Hz, 3H).

Compound 5, (rac)-Methyl 3-methyl-2,3-dihydrobenzo[b][1,4]dioxine-6-carboxylate

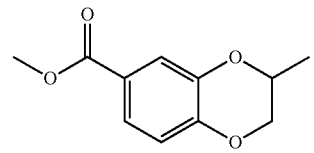

To a stirred ice cold solution of 1-chloropropan-2-ol (0.40 mL, 4.68 mmol) in DMF (20.0 mL) were added potassium carbonate (2.49 g, 18.0 mmol) and potassium iodide (0.239 g, 1.439 mmol). After 15 min, methyl 4-hydroxy-3-iodobenzoate (1.00 g, 3.60 mmol) was added and heated to reflux. After 16 hours, the reaction mixture was cooled to room temperature, diluted with ethyl acetate (10 mL) and water (10 mL). The layers were separated and the organic layer was washed with water (2×20 mL) and brine (2×20 mL). The organic layer was concentrated in vacuo and the crude product was used without further purification.

The crude product was dissolved in toluene (3 mL) and added to a dry RBF containing cesium carbonate (727 mg, 2.23 mmol), palladium(II) acetate (16.7 mg, 0.07 mmol) and 2-ditert-butylphosphino-2',4',6'-triisopropylbiphenyl (50.5 mg, 0.119 mmol) and heated to 70° C. After 16 hours the reaction mixture was cooled to room temperature and diluted with petrol. The reaction mixture was filtered through celite and concentrated in vacuo. Purification via flash column chromatography on silica gel in gradient DCM/MeOH from 0 to 5% afforded the desired product as a colourless oil (142 mg, 19%).

$^1$H NMR (500 MHz, CDCl3) δ 7.62-7.48 (m, 2H), 6.89 (d, J=8.3 Hz, 1H), 4.30-4.22 (m, 2H), 3.91-3.85 (m, 4H), 1.38 (dd, J=6.4, 2.5 Hz, 3H).

Compound 6, (rac)-3-Methyl-2,3-dihydrobenzo[b][1,4]dioxine-6-carboxylic acid

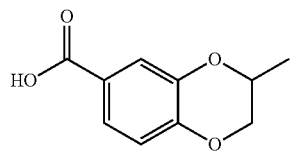

Sodium hydroxide (9.60 mg, 0.240 mmol) was added to a stirred solution of methyl 3-methyl-2,3-dihydrobenzo[b][1,4]dioxine-6-carboxylate (25 mg, 0.120 mmol) in THF (1 mL) and Water (1 mL) and heated to 70° C. After 16 hours the reaction mixture was cooled to room temperature and acidified to pH 1 using 1M solution of aqueous hydrogen chloride solution and diluted with ethyl acetate (2 mL). The layers were separated and the aqueous layer was extracted with ethyl acetate (3×2 mL). The combined organic layer with concentrated in vacuo and the crude product was used without further purification.

$^1$H NMR (500 MHz, CDCl3) δ 7.61-7.47 (m, 2H), 6.89 (d, J=8.3 Hz, 1H), 4.35-4.22 (m, 2H), 3.90 (br s, 1H), 1.37 (dd, J=6.4, 2.5 Hz, 3H).

Compound 6, N-(5-Amino-2-methylphenyl)-2-methylquinoline-6-carboxamide

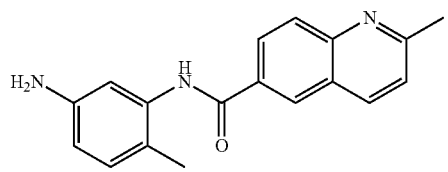 [SMILES: Cc1ccc2cc(C(=O)Nc3cc(N)ccc3C)ccc2n1]

2-Methylquinoline-6-carboxylic acid (15.0 g, 80.0 mmol) was dissolved in dry DCM (180.0 mL), DMF (0.01 mL, 0.18 mmol) and oxalyl chloride (7.40 mL, 87.0 mmol) were added drop-wise and the resulting brown/green solution was allowed to stir at 20° C. for 3 hours after which it was concentrated under vacuum to afford a dark green solid. The solid was dissolved in pyridine (120.0 mL) and 2-methyl-5-nitroaniline (11.08 g, 72.8 mmol) was added in one portion. The resulting dark brown suspension was allowed to stir for 6 days (with the addition of a further portion of acid chloride 49.3 mmol, 0.68 eq., after 5 days). The solvents were removed in vacuo and the resulting residue taken up in MeOH, then diluted with water. A precipitate formed that was collected by filtration, washed well with water, and dried under vacuum to afford the crude product as a dark brown solid, that was used directly in the next step. Crude 2-methyl-N-(2-methyl-5-nitrophenyl)quinoline-6-carboxamide (23.4 g, 72.8 mmol) was suspended in water (133.0 mL) and EtOH (400.0 mL), ammonium chloride (11.7 g, 218 mmol) and iron powder (12.2 g, 218 mmol) were added and the resulting mixture was allowed to stir at 80° C. for 18 hour. The reaction mixture was allowed to cool to room temperature, diluted with MeOH and DCM and filtered through a pad of Celite®. The filtrate was concentrated in vacuo. The resulting residue was partitioned between sat. NaHCO$_3$ (aq.) and 5% MeOH in DCM. The aqueous layer was extracted with two further portions of DCM. The combined organic layer was washed with brine, dried (MgSO$_4$) and concentrated in vacuo to afford the crude product as a dark yellow solid. The crude product was purified by column chromatography (0-10% MeOH in DCM) to afford the product as a bright yellow solid (8.14 g, 38%). $^1$H NMR (500 MHz, DMSO-d$_6$) δ 9.84 (s, 1H), 8.56 (d, J=1.8 Hz, 1H), 8.39 (d, J=8.4 Hz, 1H), 8.21 (dd, J=8.8, 1.9 Hz, 1H), 8.00 (d, J=8.8 Hz, 1H), 7.51 (d, J=8.4 Hz, 1H), 6.91 (d, J=8.2 Hz, 1H), 6.65 (d, J=2.2 Hz, 1H), 6.42 (dd, J=8.1, 2.3 Hz, 1H), 4.98 (s, 2H), 2.70 (s, 3H), 2.09 (s, 3H). HRMS (ESI$^+$): calcd for C$_{18}$H$_{18}$N$_3$O$_3$ (M+H)$^+$, 292.1444; found 292.1442.

The following compounds were synthesised according to the procedure for Example 1, by substituting the appropriate aniline for 2-methyl-5-nitroaniline.

Compound 7, N-(5-Amino-2-fluorophenyl)-2-methylquinoline-6-carboxamide

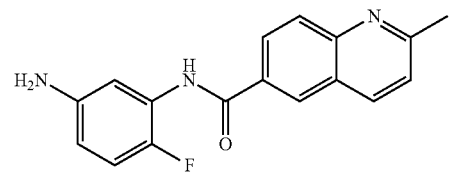 [SMILES: Cc1ccc2cc(C(=O)Nc3cc(N)ccc3F)ccc2n1]

Compound 8, N-(5-Amino-2-chlorophenyl)-2-methylquinoline-6-carboxamide

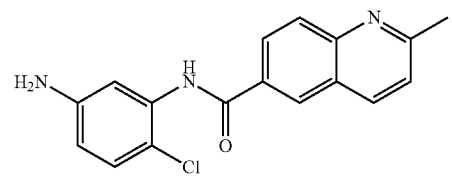 [SMILES: Cc1ccc2cc(C(=O)Nc3cc(N)ccc3Cl)ccc2n1]

TABLE A

| Compound | 1H NMR | Mass Spec |
|---|---|---|
| Compound 7 | $^1$H-NMR (500 MHz, DMSO-d$_6$) δ 10.05 (s, 1H), 8.57 (d, J = 1.7 Hz, 1H), 8.39 (d, J = 8.7 Hz, 1H), 8.19 (dd, J = 8.7, 1.7 Hz, 1H), 8.01 (d, J = 8.7 Hz, 1H), 7.52 (d, J = 8.3 Hz, 1H), 6.94 (dd, J = 9.8, 8.3 Hz, 1H), 6.89 (dd, J = 6.6, 2.7 Hz, 1H), 6.46-6.39 (m, 1H), 5.05 (br s, 2H), 2.70 (s, 3H). | HRMS (ESI$^+$): Found [M + H]$^+$ 296.1191 C$_{17}$H$_{15}$FN$_3$O requires 296.1194. |
| Compound 8 | $^1$H-NMR (500 MHz, DMSO-d$_6$): δ 9.96 (s, 1H), 8.58 (d, J = 2.2 Hz, 1H), 8.41 (d, J = 8.7 Hz, 1H), 8.21 (dd, J = 8.7, Hz, 1H), 8.02 (d, J = 8.7 Hz, 1H), 7.53 | HRMS (ESI$^+$): Found [M + H]$^+$ 312.0902 |

TABLE A-continued

| Compound | 1H NMR | Mass Spec |
|---|---|---|
| | 2.2 (d, J = 7.6 Hz, 1H), 7.15 (d, J = 8.7 Hz, 1H), 6.87 (d, J = 2.2 Hz, 1H), 6.50 (dd, J = 8.7, 2.2 Hz, 1H), 5.41 (br s, 2H), 2.70 (s, 3H). | $C_{17}H_{15}ClN_3O$ requires 312.0898. |

Example 1, N-(5-(Chroman-7-carboxamido)-2-methylphenyl)-2-methylquinoline-6-carboxamide

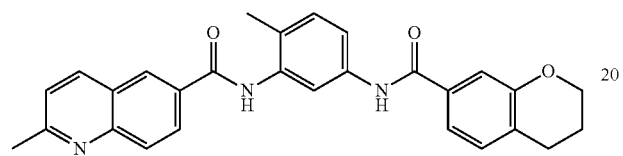

Chroman-7-carboxylic acid (75 mg, 0.42 mmol) was dissolved in anhydrous DMF (3.5 mL) at RT under $N_2$ and DIPEA (0.20 mL, 1.15 mmol) was added, followed by HATU (182 mg, 0.48 mmol). The reaction was allowed to stir for 5 min before the addition of N-(3-aminophenyl)-2-methylquinoline-6-carboxamide (111 mg, 0.38 mmol). The reaction mixture was allowed to stir for 18 h, then diluted with water. The resulting precipitate was collected by filtration and washed well with water. This material was dry-loaded onto silica and purified by Biotage chromatography using a gradient of 0-10% MeOH in DCM to afford the title compound as a white solid (51.2 mg, 30%). $^1$H NMR (500 MHz, DMSO-$d_6$) δ 10.14 (s, 1H), 10.13 (s, 1H), 8.61 (d, J=1.8 Hz, 1H), 8.41 (d, J=8.4 Hz, 1H), 8.24 (dd, J=8.8, 1.9 Hz, 1H), 8.03 (d, J=8.8 Hz, 1H), 7.89 (d, J=2.0 Hz, 1H), 7.60 (dd, J=8.3, 2.1 Hz, 1H), 7.53 (d, J=8.4 Hz, 1H), 7.43 (dd, J=7.9, 1.7 Hz, 1H), 7.36 (d, J=1.6 Hz, 1H), 7.25 (d, J=8.4 Hz, 1H), 7.19 (d, J=7.9 Hz, 1H), 4.23-4.14 (m, 2H), 2.80 (t, J=6.4 Hz, 2H), 2.71 (s, 3H), 2.25 (s, 3H), 1.97-1.91 (m, 2H). HRMS (ESI$^+$): calcd for $C_{28}H_{26}N_3O_3$ (M+H)$^+$, 452.1969; found 452.1956.

The following compounds were synthesised according to the procedure for Example 1, by substituting the appropriate carboxylic acid for chroman-7-carboxylic acid and the appropriate aniline for N-(3-aminophenyl)-2-methylquinoline-6-carboxamide.

Example 2, (rac)-2-Methyl-N-(2-methyl-5-(2-methyl-2,3-dihydrobenzofuran-6-carboxamido)phenyl)quinoline-6-carboxamide

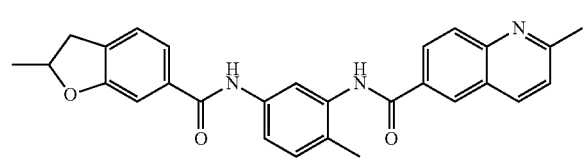

Example 3, (rac)-2-Methyl-N-(2-methyl-5-(3-methyl-2,3-dihydrobenzo[b][1,4]dioxine-6-carboxamido)phenyl)quinoline-6-carboxamide

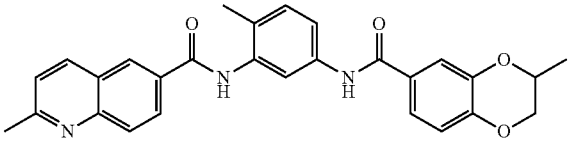

Example 4, N-(2-Fluoro-5-(3-methyl-2,3-dihydrobenzo[b][1,4]dioxine-6-carboxamido)phenyl)-2-methylquinoline-6-carboxamide

Example 5, (rac)-2-Methyl-N-(2-methyl-5-(2-methyl-2,3-dihydrobenzofuran-5-carboxamido)phenyl)quinoline-6-carboxamide

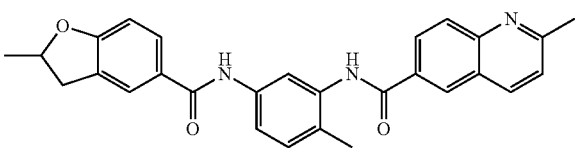

Example 6, N-(5-(Chroman-7-carboxamido)-2-fluorophenyl)-2-methylquinoline-6-carboxamide

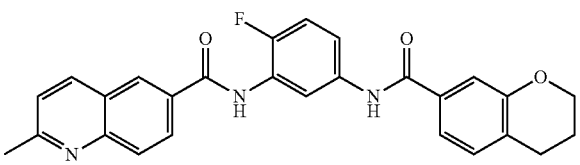 [SMILES: Cc1ccc2cc(C(=O)Nc3cc(NC(=O)c4ccc5c(c4)OCCC5)ccc3F)ccc2n1]

Example 7, N-(2-Chloro-5-(chroman-7-carboxamido)phenyl)-2-methylquinoline-6-carboxamide

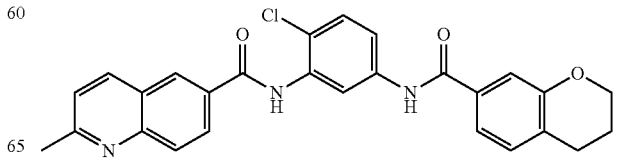

Example 8, N-(5-(Benzo[d][1,3]dioxole-5-carboxamido)-2-methylphenyl)-2-methylquinoline-6-carboxamide

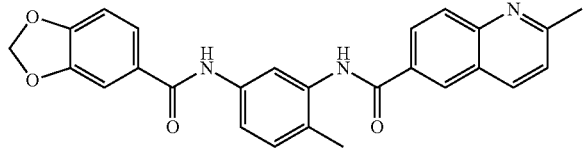 [SMILES: Cc1ccc2cc(C(=O)Nc3cc(NC(=O)c4ccc5c(c4)OCO5)ccc3C)ccc2n1]

Example 9, N-(5-(2,3-Dihydrobenzofuran-6-carboxamido)-2-methylphenyl)-2-methylquinoline-6-carboxamide

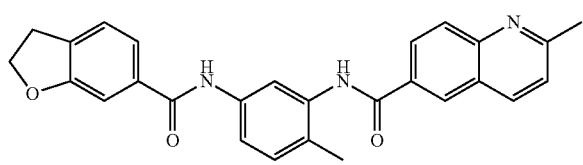 [SMILES: Cc1ccc2cc(C(=O)Nc3cc(NC(=O)c4ccc5c(c4)OCC5)ccc3C)ccc2n1]

Example 10, N-(5-(2,3-dihydrobenzofuran-5-carboxamido)-2-methylphenyl)-2-methylquinoline-6-carboxamide

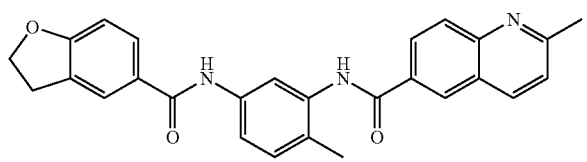 [SMILES: Cc1ccc2cc(C(=O)Nc3cc(NC(=O)c4ccc5c(c4)CCO5)ccc3C)ccc2n1]

Example 11. N-(5-(benzofuran-6-carboxamido)-2-methylphenyl)-2-methylquinoline-6-carboxamide

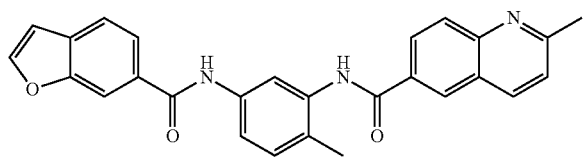 [SMILES: Cc1ccc2cc(C(=O)Nc3cc(NC(=O)c4ccc5ccoc5c4)ccc3C)ccc2n1]

Example 12. N-(5-(3,4-dihydro-2H-benzo[b][1,4]dioxepine-7-carboxamido)-2-methylphenyl)-2-methylquinoline-6-carboxamide

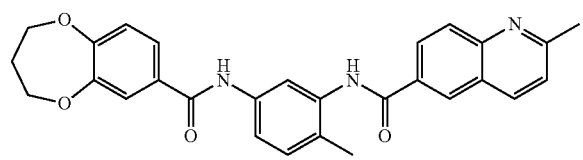 [SMILES: Cc1ccc2cc(C(=O)Nc3cc(NC(=O)c4ccc5c(c4)OCCCO5)ccc3C)ccc2n1]

TABLE B

| Compound | 1H NMR | Mass Spec |
| --- | --- | --- |
| Example 2 | $^1$H NMR (500 MHz, CDCl$_3$) δ 8.38 (br. s, 1H), 8.23-8.17 (m, 1H), 8.17-8.09 (m, 3H), 7.88 (br. s, 1H), 7.84 (br. s, 1H), 7.71 (d, J = 8.3 Hz, 1H), 7.41 (d, J = 8.4 Hz, 1H), 7.34 (dd, J = 7.7, 1.6 Hz, 1H), 7.25-7.23 (m, 2H), 5.06-4.94 (m, 1H), 3.41-3.32 (m, 1H), 2.90-2.83 (m, 1H), 2.81 (s, 3H), 2.37 (s, 3H), 1.49 (d, J = 6.3 Hz, 3H). | HRMS (ESI$^+$): calcd for C$_{28}$H$_{26}$N$_3$O$_3$ (M + H)$^+$, 452.1969; found 452.1957. |
| Example 3 | $^1$H NMR (500 MHz, DMSO-d$_6$) δ 10.13 (s, 1H), 10.06 (s, 1H), 8.61 (d, J = 2.0 Hz, 1H), 8.41 (d, J = 8.4 Hz, 1H), 8.24 (dd, J = 8.8, 2.1 Hz, 1H), 8.03 (d, J = 8.8 Hz, 1H), 7.88 (d, J = 2.2 Hz, 1H), 7.61-7.47 (m, 4H), 7.24 (d, J = 8.3 Hz, 1H), 6.99 (d, J = 8.5 Hz, 1H), 4.42-4.28 (m, 2H), 3.89 (dd, J = 11.2, 7.8 Hz, 1H), 2.71 (s, 3H), 2.24 (s, 3H), 1.32 (d, J = 6.3 Hz, 3H). | HRMS (ESI+): calcd for C$_{28}$H$_{26}$N$_3$O$_4$ (M + H)$^+$, 468.1923; found 468.1920. |
| Example 4 | $^1$H NMR (500 MHz, DMSO-d$_6$) δ 10.38 (s, 1H), 10.16 (s, 1H), 8.63 (d, J = 2.0 Hz, 1H), 8.45 (d, J = 8.5 Hz, 1H), 8.24 (d, J = 8.8 Hz, 1H), 8.14 (dd, J = 7/0, 2.7 Hz, 1H), 8.04 (d, J = 8.8 Hz, 1H), 7.65 (ddd, J = 9.0, 4.3, 2.7 Hz, 1H), 7.60-1.49 (m, 3H), 7.29 (dd, J = 10.1, 9.0 Hz, 1H), 7.00 (d, J = 8.4 Hz, 1H), 4.42-4.27 (m, 2H), 3.90 (dd, J = 11.3, 7.8 Hz, 1H), 2.71 (s, 3H), 1.32 (d, J = 6.3 Hz, 3H). | HRMS (ESI+): calcd for C$_{27}$H$_{23}$N$_3$O$_4$F (M + H)$^+$, 472.1673; found 472.1670. |
| Example 5 | $^1$H NMR (500 MHz, DMSO-d$_6$) δ 10.14 (s, 1H), 10.04 (s, 1H), 8.61 (d, J = 1.7 Hz, 1H), 8.41 (d, J = 8.4 Hz, 1H), 8.24 (dd, J = 8.8, 1.9 Hz, 1H), 8.03 (d, J = 8.8 Hz, 1H), 7.88 (d, J = 2.0 Hz, 1H), 7.86 (br s, 1H), 7.79 (dd, J = 8.4, 1.7 Hz, 2H), 7.58 (dd, J = 8.3, 2.1 Hz, 1H), 7.53 (d, J = 8.4 Hz, 1H), 7.24 (d, J = 8.4 Hz, 1H), 6.84 (d, J = 8.4 Hz, 1H), 5.09-4.91 (m, 1H), 3.39 (dd, J = 15.9, 8.9 Hz, 1H), 2.85 (dd, J = 15.8, 7.4 Hz, 1H), 2.71 (s, 3H), 2.24 (s, 3H), 1.41 (d, J = 6.2 Hz, 3H). | HRMS (ESI$^+$) calcd for C$_{28}$H$_{26}$N$_3$O$_3$ (M + H)$^+$, 452.1969; found 452.1956. |
| Example 6 | $^1$H NMR (500 MHz, DMSO-d$_6$) δ 10.37 (s, 1H), 10.24 (s, 1H), 8.62 (d, J = 1.9 Hz, 1H), 8.41 (d, J = 8.4 Hz, 1H), 8.23 (dd, J = 8.8, 2.0 Hz, 1H), 8.15 (dd, J = 7.0, 2.6 Hz, 1H), 8.03 (d, J = 8.8 Hz, 1H), 7.66 (ddd, J = 8.9, 4.2, 2.7 Hz, 2H), 7.53 (d, J = 8.4 Hz, 1H), 7.44 (dd, J = 7.9, 1.8 Hz, 1H), 7.36 (d, J = 1.8 Hz, 1H), 7.32-7.27 (m, 1H), 7.21 (d, J = 7.9 Hz, 1H), 4.23-4.15 (m, 2H), 2.81 (t, J = 6.4 Hz, 2H), 2.71 (s, 3H), 1.98-1.92 (m, 2H). | calcd for C$_{27}$H$_{23}$ClN$_3$O$_3$ (M + H)$^+$, 456.1718; found 456.1710 |
| Example 7 | $^1$H NMR (500 MHz, DMSO-d$_6$) δ 10.32 (s, 1H), 10.31 (s, 1H), 8.63 (d, J = 1.9 Hz, 1H), 8.42 (d, J = 8.5 Hz, 1H), 8.24 (dd, J = 8.8, 2.0 Hz, 1H), 8.15 (dd, J = 2.5 Hz, 1H), 8.04 (d, J = 8.8 Hz, 1H), 7.75 (dd, J = 8.8, 2.5 Hz, 1H), 7.54 (d, J = 8.7 Hz, 2H), 7.44 (dd, J = 7.9, 1.8 Hz, 1H), 7.37 (d, J = 1.8 Hz, 1H), 7.21 (d, J = 7.9 Hz, 1H), 4.23-4.13 (m, 2H), 2.81 (t, J = 6.4 Hz, 2H), 2.71 (s, 3H), 1.95 (dt, J = 11.5, 6.3 Hz, 2H). | HRMS (ESI+): calcd for C$_{27}$H$_{23}$ClN$_3$O$_3$ (M + H)$^+$, 472.1422; found 472.1407. |
| Example 8 | $^1$H NMR (500 MHz, DMSO-d$_6$) δ 10.13 (s, 1H), 10.09 (s, 1H), 8.63-8.60 (br m, 1H), 8.41 (d, J = 8.4 Hz, 1H), 8.24 (dd, J = 8.8, 1.7 Hz, 1H), 8.03 (d, J = 8.7 Hz, 1H), 7.88-7.86 (m, 1H), 7.59 (dd, J = 8.2, 1.5 Hz, 2H), 7.53 (dd, J = 4.9, 3.4 Hz, 2H), 7.25 (d, J = 8.4 Hz, 1H), 7.06 (d, J = 8.2 Hz, 1H), 6.13 (s, 2H), 2.71 (s, 3H), 2.25 (s, 3H). | HRMS (ESI$^+$): calcd for C$_{26}$H$_{22}$N$_3$O$_4$ (M + H)$^+$, 440.1605; found 440.1589. |
| Example 9 | $^1$H-NMR (500 MHz, DMSO-d$_6$): δ 10.14 (app. s, 2H), 8.60 (s, 1H), 8.41 (d, J = 8.1 Hz, 1H), 8.24 (dd, J = 9.4, 1.3 | HRMS (ESI$^+$): calcd for C$_{27}$H$_{24}$N$_3$O$_2$ |

TABLE B-continued

| Compound | 1H NMR | Mass Spec |
|---|---|---|
| | Hz, 1H), 8.03 (d, J = 8.1 Hz, 1H), 7.88 (s, 1H), 7.59 (dd, J = 8.1, 1.3 Hz, 1H), 7.53 (d, J = 9.4 Hz, 1H), 7.48 (d, J = 8.1 Hz, 1H), 7.36 (d, J = 8.1 Hz, 1H), 7.34 (s, 1H), 7.25 (d, J = 9.4 Hz, 1H), 4.59 (t, J = 8.1 Hz, 2H), 3.25 (t, J = 8.1 Hz, 2H), 2.71 (s, 3H), 2.25 (s, 3H). | (M + H)+, 438.1812; found 438.1824. |
| Example 10 | $^1$H-NMR (500 MHz, DMSO-$d_6$): δ 10.14 (s, 1H), 10.06 (s, 1H), 8.61 (d, J = 15 Hz, 1H), 8.41 (d, J = 8.9 Hz, 1H), 8.24 (dd, J = 8.9, 1.5 Hz, 1H), 8.03 (d, J = 8.9 Hz, 1H), 7.90-7.87 (m, 2H), 7.80 (dd, J = 8.9, 1.5 Hz, 1H), 7.59 (dd, J = 8.9, 1.5 Hz, 1H), 7.53 (d, J = 8.9 Hz, 1H), 7.24 (d, J = 7.4 Hz, 1H), 6.87 (d, J = 8.9 Hz, 1H), 4.62 (t, J = 8.9 Hz, 2H), 3.25 (t, J = 8.9 Hz, 2H), 2.71 (s, 3H), 2.25 (s, 3H). | HRMS (ESI+): calcd for $C_{27}H_{24}N_3O_2$ (M + H)+, 438.1812; found 438.1809. |
| Example 11 | $^1$H-NMR (500 MHz, DMSO-$d_6$): δ 10.30 (s, 1H), 10.15 (s, 1H), 8.61 (d, J = 1.9 Hz, 1H), 8.41 (d, J = 8.9 Hz, 1H), 8.27-8.23 (m, 2H), 8.18 (d, J = 2.5 Hz, 1H), 8.03 (d, J = 8.7 Hz, 1H), 7.94-7.89 (m, 2H), 7.79 (d, J = 8.7 Hz, 1H), 7.64 (dd, J = 8.7, 1.9 Hz, 1H), 7.53 (d, J = 7.8 Hz, 1H), 7.28 (d, J = 8.7 Hz, 1H), 7.08 (dd, J = 2.6, 1.0 Hz, 1H), 2.71 (s, 3H), 2.26 (s, 3H). | HRMS (ESI+): calcd for $C_{27}H_{22}N_3O_3$ (M + H)+, 436.1661; found 436.1670. |
| Example 12 | $^1$H-NMR (500 MHz, DMSO-$d_6$): δ 10.14 (s, 1H), 10.13 (s, 1H), 8.61 (s, 1H), 8.41 (d, J = 8.2 Hz, 1H), 8.25 (dd, J = 8.2, 2.3 Hz, 1H), 8.04 (d, J = 8.2 Hz,1 H), 7.88 (d, J = 2.3 Hz, 1H), 7.63 (d, J = 2.3 Hz, 1H), 7.62-7.53 (m, 2H), 7.53 (d, J = 8.2 Hz, 1H), 7.25 (d, J = 8.2 Hz, 1H), 7.07 (d, J = 8.2 Hz, 1H), 4.25-4.16 (m, 4H), 2.71 (s, 3H), 2.24 (s, 3H), 2.15 (m, 2H). | HRMS (ESI+): calcd for $C_{28}H_{26}N_3O_4$ (M + H)+, 468.1917; found 468.1918. |

Example 13, N-(5-(2,3-Dihydrobenzofuran-6-carboxamido)-2-fluorophenyl)-2-methylquinoline-6-carboxamide

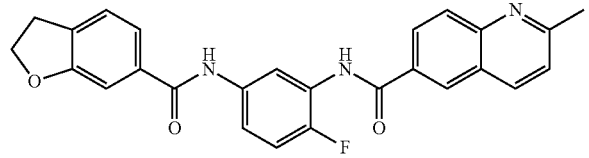 [SMILES: Cc1ccc2cc(C(=O)Nc3cc(NC(=O)c4ccc5c(c4)OCC5)ccc3F)ccc2n1]

2,3-Dihydrobenzofuran-6-carboxylic acid (100.0 mg, 0.611 mmol) was dissolved in dry DCM (2.0 mL), DMF (0.11 µL, 1.430 µmol) and oxalyl chloride (0.06 mL, 0.709 mmol) were added drop-wise and the resulting very pale yellow-green solution was allowed to stir at 20° C. for 3 hours after which it was concentrated under vacuum to afford a dry pale yellow solid. The solid was dissolved in pyridine (2.0 mL) and N-(5-amino-2-fluorophenyl)-2-methylquinoline-6-carboxamide (164.0 mg, 0.555 mmol) was added in one portion. The resulting dark brown suspension was allowed to stir for 18 hours after which it was poured onto water (2 mL) and the resulting precipitate was filtered and washed with water (3×5 mL). The light brown solid crude product was purified via flash column chromatography on silica gel in gradient from 0 to 2% MeOH in DCM to afford the title compound as a white solid (155.0 mg, 63.2%). $^1$H-NMR (500 MHz, DMSO-$d_6$): δ10.40 (s, 1H), 10.27 (s, 1H), 8.62 (d, J=1.2 Hz, 1H), 8.42 (d, J=8.1 Hz, 1H), 8.23 (dd, J=8.1, 1.2 Hz, 1H), 8.14 (dd, J=7.0, 2.3 Hz, 1H), 8.03 (d, J=8.1 Hz, 1H), 7.69-7.63 (m, 1H), 7.54 (d, J=8.1 Hz, 1H), 7.48 (dd, J=8.1, 2.3 Hz, 1H), 7.37 (d, J=7.0 Hz, 1H), 7.35 (d, J=2.3 Hz, 1H), 7.30 (app t, J=9.3 Hz, 1H), 4.60 (t, J=8.1 Hz, 2H), 3.25 (t, J=8.1 Hz, 2H), 2.71 (s, 3H). HRMS (ESI+): calcd for $C_{26}H_{21}FN_3O_3$ (M+H)+, 442.1567; found 442.1570.

The following compound was synthesised according to the procedure for Example 13, by substituting the appropriate aniline for N-(5-amino-2-fluorophenyl)-2-methylquinoline-6-carboxamide.

Example 14, N-(2-Chloro-5-(2,3-dihydrobenzofuran-6-carboxamido)phenyl)-2-methylquinoline-6-carboxamide

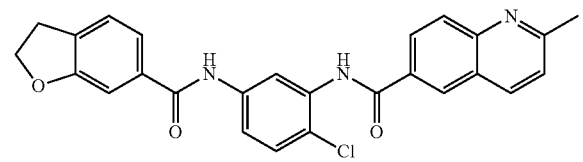 [SMILES: Cc1ccc2cc(C(=O)Nc3cc(NC(=O)c4ccc5c(c4)OCC5)ccc3Cl)ccc2n1]

TABLE C

| Compound | 1H NMR | Mass Spec |
|---|---|---|
| Example 14 | $^1$H-NMR (500 MHz, DMSO-$d_6$): δ 10.34 (s, 1H), 10.32 (s, 1H), 8.63 (br s, 1H), 8.42 (d, J =60 8.4 Hz, 1H), 8.24 (d, J = 8.4 Hz, 1H), 8.14 (br s, 1H), 8.04 (d, J = 8.4 Hz, 1H), 7.75 (d, J = 8.4 Hz, 1H), 7.54 (d, J = 8.4 Hz, 2H), 7.48 (d, J = 6.8 Hz, 1H), 7.38 (d, J = 6.8 Hz, 1H), 7.35 (br s, 1H), 4.60 (t, J = 8.4 Hz, 2H), 3.25 (t, J = 8.4 Hz, 2H), 2.71 (s, 3H). | HRMS (ESI+): calcd for $C_{26}H_{21}ClN_3O_3$ (M + H)+, 458.1271; found 458.1280. |

Example 15, N-(5-(Chroman-7-carboxamido)-2-fluorophenyl)-2-((4-ethylpiperazin-1-yl)methyl)quinoline-6-carboxamide

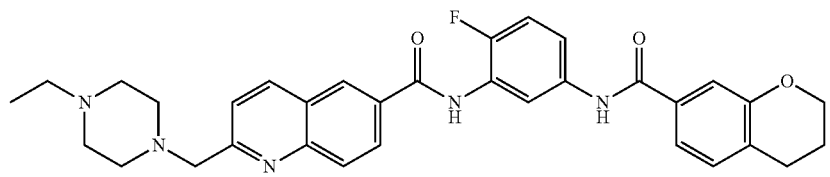 [SMILES: CCN1CCN(Cc2ccc3cc(C(=O)Nc4cc(NC(=O)c5ccc6c(c5)OCCC6)ccc4F)ccc3n2)CC1]

N-(5-(Chroman-7-carboxamido)-2-fluorophenyl)-2-methylquinoline-6-carboxamide (205 mg, 0.45 mmol) was dissolved in a mixture of anhydrous dioxane (4.0 mL) and anhydrous DMF (0.4 mL). Selenium dioxide (55 mg, 0.50 mmol) was added and the reaction heated to 80° C. for 3 h. The reaction was allowed to cool and was filtered through Celite® eluting with DCM. The solvents were removed in vacuo (using co-evaporation with heptane to remove traces of DMF). This material was used as crude directly in the next reaction.

The crude aldehyde (211 mg, 0.45 mmol) was suspended in anhydrous DCM (5 mL) at RT under $N_2$. 1-Ethylpiperazine (0.17 ml, 1.35 mmol) was added and the reaction allowed to stir for 18 h. Sodium triacetoxyborohydride (286 mg, 1.35 mmol) was added and the reaction allowed to stir for 4 h. The reaction mixture was quenched with sat. aq. $NaHCO_3$ (15 mL) and the aqueous layer extracted with 10% MeOH in DCM (3×15 mL). The combined organic layer was dried ($Na_2SO_4$) and concentrated in vacuo. The material was dry-loaded onto silica and purified by biotage chromatography using a gradient of 0-10% MeOH in DCM. The material was further purified by SCX chromatography (eluting with MeOH, followed by 10% 2M $NH_3$ in MeOH/MeOH), then triturated with ether to afford the title compound as an off-white solid (55.6 mg, 22%). $^1$H NMR (500 MHz, DMSO-$d_6$) b 10.39 (s, 1H), 10.24 (s, 1H), 8.65 (d, J=1.9 Hz, 1H), 8.49 (d, J=8.5 Hz, 1H), 8.25 (dd, J=8.8, 2.0 Hz, 1H), 8.15 (dd, J=7.0, 2.6 Hz, 1H), 8.08 (d, J=8.8 Hz, 1H), 7.73 (d, J=8.5 Hz, 1H), 7.66 (ddd, J=8.9, 4.2, 2.7 Hz, 1H), 7.44 (dd, J=7.9, 1.8 Hz, 1H), 7.36 (d, J=1.8 Hz, 1H), 7.33-7.27 (m, 1H), 7.21 (d, J=7.9 Hz, 1H), 4.25-4.12 (m, 2H), 3.79 (s, 2H), 2.81 (t, J=6.4 Hz, 2H), 2.52-2.35 (br m, 8H), 2.31 (q, J=7.2 Hz, 2H), 1.98-1.92 (m, 2H), 0.98 (t, J=7.2 Hz, 3H). HRMS (ESI$^+$): calcd for $C_{33}H_{35}FN_5O_3$ (M+H)$^+$, 568.2718; found 568.2705.

The following compounds were synthesised according to the procedure for Example 15, by substituting the appropriate amine for 1-ethylpiperazine and the appropriate carboxamide for N-(5-(chroman-7-carboxamido)-2-fluorophenyl)-2-methylquinoline-6-carboxamide.

Example 16, N-(5-(2,3-Dihydrobenzofuran-6-carboxamido)-2-methylphenyl)-2-((4-ethylpiperazin-1-yl)methyl)quinoline-6-carboxamide

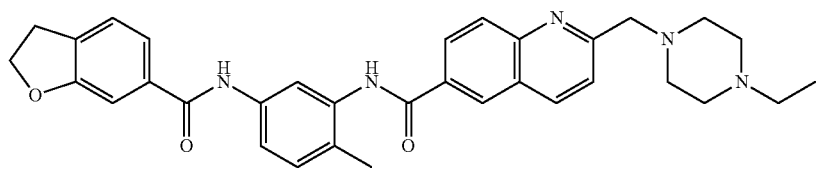 [SMILES: CCN1CCN(Cc2ccc3cc(C(=O)Nc4cc(NC(=O)c5ccc6c(c5)OCC6)ccc4C)ccc3n2)CC1]

Example 17, N-(5-(2,3-Dihydrobenzofuran-6-carboxamido)-2-fluorophenyl)-2-((4-ethylpiperazin-1-yl)methyl)quinoline-6-carboxamide

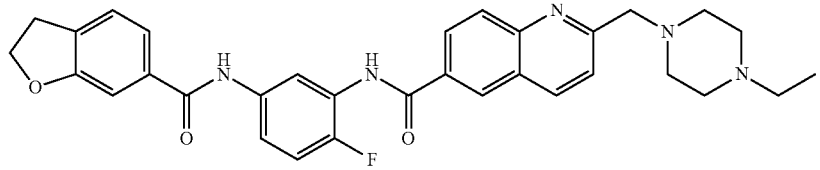

Example 18, N-(2-Chloro-5-(2,3-dihydrobenzofuran-6-carboxamido)phenyl)-2-((4-ethylpiperazin-1-yl)methyl)quinoline-6-carboxamide

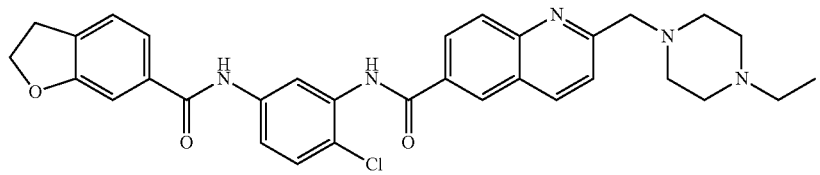 [SMILES: CCN1CCN(Cc2ccc3cc(C(=O)Nc4cc(NC(=O)c5ccc6c(c5)OCC6)ccc4F)ccc3n2)CC1]

Example 19, 2-(Azetidin-1-ylmethyl)-N-(5-(2,3-dihydrobenzofuran-6-carboxamido)-2-fluorophenyl)quinoline-6-carboxamide

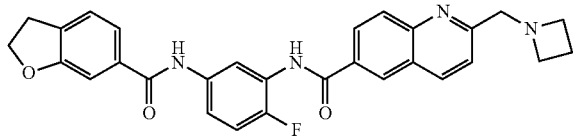 [SMILES: O=C(Nc1ccc(F)c(NC(=O)c2ccc3nc(CN4CCC4)ccc3c2)c1)c1ccc2c(c1)OCC2]

Example 20, 2-(Azetidin-1-ylmethyl)-N-(2-chloro-5-(chroman-7-carboxamido)phenyl)quinoline-6-carboxamide

N-(2-Chloro-5-(chroman-7-carboxamido)phenyl)-2-methylquinoline-6-carboxamide (228 mg, 0.48 mmol) was dissolved in a mixture of anhydrous dioxane (2.5 mL) and anhydrous DMF (2.5 mL). Selenium dioxide (59 mg, 0.53 mmol) was added and the reaction allowed to stir at RT under $N_2$ for 2 days [with addition of two further portions of selenium dioxide (27 mg, 0.24 mmol)]. The reaction was filtered through celite, eluting with DCM. The solvents were removed in vacuo (using co-evaporation with heptane to remove traces of DMF). This material was used as crude directly in the next reaction.

The crude aldehyde (235 mg, 0.48 mmol) was suspended in anhydrous MeOH (5 ml) at RT under $N_2$. Azetidine hydrochloride (47 mg, 0.51 mmol) was added, followed by sodium cyanoborohydride (33 mg, 0.53 mmol) and the reaction allowed to stir at RT for 18 h. The solvent was removed in vacuo and the resulting residue taken up in 10% MeOH/DCM. The organic layer was washed with 1 M NaOH aq. and dried ($Na_2SO_4$). The material was dry-loaded onto silica and purified by biotage chromatography using a gradient of 0-10% MeOH in DCM. The material was further purified by SCX chromatography (eluting with MeOH, followed by 10% 2M $NH_3$ in MeOH/MeOH), then triturated with ether to afford the title compound as a yellow solid (10.6 mg, 4%). $^1$H NMR (500 MHz, DMSO-$d_6$) δ 10.32 (app. br s, 2H), 8.65 (s, 1H), 8.48 (d, J=8.5 Hz, 1H), 8.27-8.24 (m, 1H), 8.15 (d, J=2.2 Hz, 1H), 8.08 (d, J=8.8 Hz, 1H), 7.75 (dd, J=8.8, 2.2 Hz, 1H), 7.65 (d, J=8.5 Hz, 1H), 7.54 (d, J=8.8 Hz, 1H), 7.44 (d, J=7.8 Hz, 1H), 7.37 (s, 1H), 7.21 (d, J=7.8 Hz, 1H), 4.24-4.15 (m, 2H), 3.88 (s, 2H), 3.28 (t, J=6.9 Hz, 4H), 2.81 (t, J=6.2 Hz, 2H), 2.05 (p, J=7.0 Hz, 2H), 1.95 (dt, J=10.6, 5.8 Hz, 2H). HRMS (ESI$^+$): calcd for $C_{30}H_{28}ClN_4O_3$ (M+H)$^+$, 527.1844; found 527.1828.

The following compound was synthesised according to the procedure for Example 20, by substituting the appropriate carboxamide for N-(2-chloro-5-(chroman-7-carboxamido)phenyl)-2-methylquinoline-6-carboxamide.

Example 21, 2-(azetidin-1-ylmethyl)-N-(5-(2,3-dihydrobenzofuran-6-carboxamido)-2-fluorophenyl)quinoline-6-carboxamide

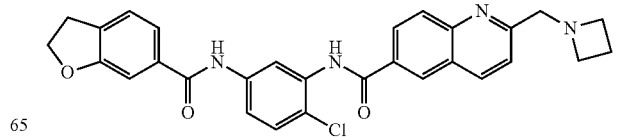

TABLE D

| Compound | 1H NMR | Mass Spec |
|---|---|---|
| Example 16 | $^1$H NMR (500 MHz, DMSO-$d_6$) δ 10.15 (s, 1H), 10.14 (s, 1H), 8.63 (d, J = 1.8 Hz, 1H), 8.48 (d, J = 8.4 Hz, 1H), 8.26 (dd, J = 8.8, 2.0 Hz, 1H), 8.08 (d, J = 8.8 Hz, 1H), 7.89 (d, J = 2.1 Hz, 1H), 7.72 (d, J = 8.5 Hz, 1H), 7.60 (dd, J = 8.3, 2.1 Hz, 1H), 7.48 (dd, J = 7.7, 1.5 Hz, 1H), 7.36 (d, J = 7.8 Hz, 1H), 7.34 (d, J = 1.3 Hz, 1H), 7.25 (d, J = 8.5 Hz, 1H), 4.59 (t, J = 8.7 Hz, 2H), 3.79 (s, 2H), 3.25 (t, J = 8.7 Hz, 2H), 2.50-2.35 (br m, 8H), 2.31 (q, J = 7.2 Hz, 2H), 2.25 (s, 3H), 0.98 (t, J = 7.2 Hz, 3H). | HRMS (ESI$^+$): calcd for $C_{33}H_{36}N_5O_3$ (M + H)$^+$, 550.2813; found 550.2800. |
| Example 17 | $^1$H-NMR (500 MHz, DMSO-$d_6$): δ 10.40 (s, 1H), 10.25 (s, 1H), 8.65 (d, J = 1.7 Hz, 1H), 8.49 (d, J = 8.7 Hz, 1H), 8.25 (dd, J = 8.7, 1.7 Hz, 1H), 8.15 (dd, J = 6.9, 2.6 Hz, 1H), 8.08 (d, J = 8.7 Hz, 1H), 7.73 (d, J = 7.8 Hz, 1H), 7.69-7.64 (m, 1H), 7.48 (dd, J = 8.7, 1.7 Hz, 1H), 7.38 (d, J = 7.8 Hz, 1H), 7.35 (d, J = 1.7 Hz, 1H), 7.31 (dd, J = 8.7, 7.8 Hz, 1H), 4.60 (t, J = 8.7 Hz, 2H), 3.79 (br s, 2H), 3.25 (t, J = 8.7 Hz, 2H), 2.50-2.36 (m, 8H), 2.32 (q, J = 8.7 Hz, 2H), 0.99 (t, J = 8.7 Hz, 3H). | HRMS (ESI$^+$): calcd for $C_{32}H_{33}FN_5O_3$ (M + H)$^+$, 554.2562; found 554.2557. |
| Example 18 | $^1$H-NMR (500 MHz, DMSO-$d_6$): δ 10.33 (app. s, 2H), 8.65 (br s, 1H), 8.50 (d, J = 8.6 Hz, 1H), 8.26 (dd, J = 8.6, 2.1 Hz, 1H), 8.16 (d, J = 2.1 Hz, 1H), 8.09 (d, J = 8.6 Hz, 1H), 7.78-7.60 (m, 2H), 7.54 (d, J = 8.6 Hz, 1H), 7.49 (d, J = 6.4 Hz, 1H), 7.38 (d, J = 7.5 Hz, 1H), 7.35 (br s, 1H), 4.60 (t, J = 8.6 Hz, 2H), 3.81 (br s, 2H), 3.25 (t, J = 8.6 Hz, 2H), 2.50-2.28 (m, 10H), 1.00 (bt, J = 8.6 Hz, 3H). | HRMS (ESI$^+$): calcd for $C_{32}H_{33}ClN_5O_3$ (M + H)$^+$, 570.2266; found 570.2254. |
| Example 19 | $^1$H-NMR (500 MHz, CD$_3$OD): δ 8.61 (d, J = 2.2 Hz, 1H), 8.52 (d, J = 8.7 Hz, 1H), 8.31 (dd, J = 8.7, 2.2 Hz, 1H), 8.23 (dd, J = 7.3, 2.9 Hz, 1H), 8.19 (d, J = 8.7 Hz, 1H), 7.62 (d, J = 8.7 Hz, 1H), 7.61-7.57 (m, 1H), 7.46 (d, J = 7.3, 2.2 Hz, 1H), 7.35 (d, J = 7.3 Hz, 1H), 7.30 (d, J = 1.5 Hz, 1H), 7.25 (dd, J = 8.7, 9.4 Hz, 1H), 4.63 (t, J = 8.7 Hz, 2H), 4.25 (br s, 2H), 3.93 (br s, 4H), 3.29 (t, J = 8.7 Hz, 2H), 2.43 (quin., J = 7.3 Hz, 2H). | HRMS (ESI$^+$): calcd for $C_{29}H_{25}FN_4O_3$ (M + H)$^+$, 497.1989; found 497.2000. |

TABLE E

| Compound | 1H NMR | Mass Spec |
|---|---|---|
| Example 21 | $^1$H-NMR (500 MHz, CD$_3$OD): δ 8.62 (d, J = 1.9 Hz, 1H), 8.50 (d, J = 8.3 Hz, 1H), 8.31 (dd, J = 8.7, 1.9 Hz, 1H), 8.25 (d, J = 2.4 Hz, 1H), 8.17 (d, J = 9.1 Hz, 1H), 7.68 (dd, J = 8.7, 2.4 Hz, 1H), 7.65 (d, J = 8.3 Hz, 1H), 7.52 (d, J = 8.7 Hz, 1H), 7.46 (dd, J = 7.5, 1.6 Hz, 1H), 7.35 (d, J = 7.9 Hz, 1H), 7.30 (d, J = 1.6 Hz, 1H), 4.63 (t, J = 8.7 Hz, 2H), 4.16 (s, 2H), 3.65 (br t, J = 7.5 Hz, 4H), 3.29 (t, J = 8.3 Hz, 2H), 2.29 (quin., J = 7.5 Hz, 2H). | HRMS (ESI$^+$): calcd for C$_{29}$H$_{26}$ClN$_4$O$_3$ (M + H)$^+$, 513.1690; found 513.1693. |

Biological Activity

The exemplified compounds above were tested in the Cellisa assay described above in the biological assay section. The following data was obtained:

| Example No. | SKOV3 Cellisa (μM) |
|---|---|
| 1 | 0.38 |
| 2 | 3.4 |
| 3 | 4.1 |
| 4 | 8.8 |
| 5 | 2.9 |
| 6 | 2.7 |
| 7 | 1.5 |
| 8 | 0.13 |
| 9 | 0.17 |
| 10 | 1.8 |
| 11 | 0.88 |
| 12 | 0.67 |
| 13 | 1.8 |
| 14 | 2.1 |
| 15 | 1 |
| 16 | 0.12 |
| 17 | 0.78 |
| 18 | 0.64 |
| 19 | 3.1 |
| 20 | 3.8 |
| 21 | 1.8 |

REFERENCES

1. Altenbach, R. J.; Black, L. A.; Chang, S.-j.; Cowart, M. D.; Faghih, R.; Gfesser, G. A.; Ku, Y.-y.; Liu, H.; Lukin, K. A.; Nersesian, D. L.; Pu, Y.-m.; Sharma, P. N.; Bennani, Y. L. Preparation of pyrrolidine derivatives as histamine-3 receptor ligands. US20040092521A1, 2004.
2. Sagi, K.; Fujita, K.; Sugiki, M.; Takahashi, M.; Takehana, S.; Tashiro, K.; Kayahara, T.; Yamanashi, M.; Fukuda, Y.; Oono, S.; Okajima, A.; Iwata, S.; Shoji, M.; Sakurai, K., Optimization of a coagulation factor VIIa inhibitor found in factor Xa inhibitor library. Bioorganic & Medicinal Chemistry 2005, 13 (5), 1487-1496.
3. Giardina, G.; Clarke, G. D.; Dondio, G.; Petrone, G.; Sbacchi, M.; Vecchietti, V., Selective .kappa.-Opioid Agonists: Synthesis and Structure-Activity Relationships of Piperidines Incorporating an Oxo-Containing Acyl Group. Journal of Medicinal Chemistry 1994, 37(21), 3482-3491.
4. Wishka, D. G.; Walker, D. P.; Yates, K. M.; Reitz, S. C.; Jia, S.; Myers, J. K.; Olson, K. L.; Jacobsen, E. J.; Wolfe, M. L.; Groppi, V. E.; Hanchar, A. J.; Thornburgh, B. A.; Cortes-Burgos, L. A.; Wong, E. H. F.; Staton, B. A.; Raub, T. J.; Higdon, N. R.; Wall, T. M.; Hurst, R. S.; Walters, R. R.; Hoffmann, W. E.; Hajos, M.; Franklin, S.; Carey, G.; Gold, L. H.; Cook, K. K.; Sands, S. B.; Zhao, S. X.; Soglia, J. R.; Kalgutkar, A. S.; Arneric, S. P.; Rogers, B. N., Discovery of N-[(3R)-1-Azabicyclo[2.2.2]oct-3-yl]furo[2,3-c]pyridine-5-carboxamide, an Agonist of the α7 Nicotinic Acetylcholine Receptor, for the Potential Treatment of Cognitive Deficits in Schizophrenia: Synthesis and Structure-Activity Relationship. Journal of Medicinal Chemistry 2006, 49 (14), 4425-4436.
5. Nagase, T.; Mizutani, T.; Ishikawa, S.; Sekino, E.; Sasaki, T.; Fujimura, T.; Ito, S.; Mitobe, Y.; Miyamoto, Y.; Yoshimoto, R.; Tanaka, T.; Ishihara, A.; Takenaga, N.; Tokita, S.; Fukami, T.; Sato, N., Synthesis, Structure-Activity Relationships, and Biological Profiles of a Quinazolinone Class of Histamine H3 Receptor Inverse Agonists. Journal of Medicinal Chemistry 2008, 51 (15), 4780-4789.
6. Boys, M. L.; Bradley, M.; Delisle, R. K.; Hennings, D. D.; Kennedy, A. L.; Marmsater, F. P.; Medina, M.; Munson, M. C.; Rast, B.; Rizzi, J. P.; Rodriguez, M. E.; Topalov, G. T.; Zhao, Q. Preparation of substituted N-(1H-indazol-4-yl)imidazo[1,2-a]pyridine-3-carboxamides as cFMS inhibitors. WO2011079076A1, 2011.
7. Kahraman, M.; Govek, S. P.; Nagasawa, J. Y.; Smith, N. D. Preparation of chromen-6-ol derivatives as modulators of estrogen receptor. WO2011156518A2, 2011.
8. Radford, P.; Attygalle, A. B.; Meinwald, J.; Smedley, S. R.; Eisner, T., Pyrrolidinoöxazolidine Alkaloids from Two Species of Ladybird Beetles1. Journal of Natural Products 1997, 60 (8), 755-759.
9. Azizi, N.; Saidi, M. R., Highly Chemoselective Addition of Amines to Epoxides in Water. Organic Letters 2005, 7 (17), 3649-3651.
10. Bai, H.; Bailey, S.; Bhumralkar, D. R.; Bi, F.; Guo, F.; He, M.; Humphries, P. S.; Ling, A. L.; Lou, J.; Nukui, S.; Zhou, R. Preparation of fused phenyl amido heterocycles for the prevention and treatment of glucokinase-mediated diseases. WO2007122482A1, 2007.

The invention claimed is:

1. A compound of formula Ia shown below, or a pharmaceutically acceptable salt thereof:

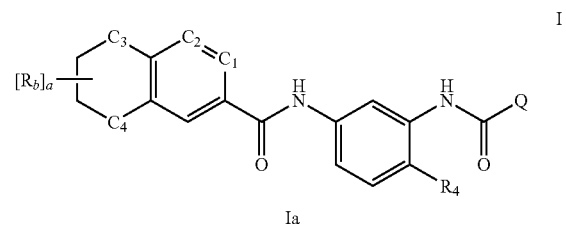

Ia wherein:
C$_1$ is CR$_{a1}$;
C$_2$ is CR$_{a2}$;
R$_{a1}$ and R$_{a2}$ are each independently selected from hydrogen, fluoro, chloro, cyano, (1-2C)alkyl, (1-2C)alkoxy or (1-2C)haloalkyl;
C$_3$ is O or CH;
C$_4$ is O or CH;
a is 0, 1 or 2;
R$_b$ is fluoro or (1-2C)alkyl;
subject to the proviso that:
(i) one or two of C$_3$ or C$_4$ are oxygen; and
(i) when C$_3$ and C$_4$ are both oxygen then a is 1 or 2;

R₄ is selected from hydrogen, fluoro, chloro, bromo, iodo, CF₃, OCF₃, cyano, NO₂, (1-4C)alkyl, (1-4C)alkoxy, or a group of the formula:

W—X—Y—Z wherein:
W is absent or (1-3C)alkylene;
X is —O— or —N(R⁴⁰)—, wherein R⁴⁰ is selected from hydrogen or (1-2C)alkyl;
Y is absent or a (1-3C)alkylene;
Z is hydrogen, (1-6C)alkyl, (3-6C)cycloalkyl or a 4 to 10-membered monocyclic or bicyclic heterocyclic ring;
or Y and Z are linked with R⁴⁰ such that, together with the nitrogen atom to which they are attached, they form 4 to 10-membered monocyclic or bicyclic heterocyclic ring;
and wherein any alkylene, alkyl, cycloalkyl or heterocyclyl group present in a R₄ substituent group is optionally further substituted by one or more substituent groups independently selected from oxo, halo, nitro, hydroxy, cyano, carboxy, -M-NR⁴¹R⁴², -M-S(O)$_d$R⁴¹, -M-C(O)NR⁴¹R⁴², -M-NR⁴¹C(O)R⁴², -M-NR⁴¹S(O)₂R⁴², -M-S(O)₂NR⁴¹R⁴², (1-5C)alkyl, (1-5C)alkoxy, (1-5C)haloalkyl, (1-5C)haloalkoxy or (1-5C)alkanoyl, and wherein M is absent or (1-4C)alkylene, and R⁴¹ and R⁴² are each independently selected from hydrogen or (1-5C)alkyl; or R⁴¹ and R⁴² can be linked such that, together with the nitrogen atom to which they are attached, they form a 4-6 membered heterocyclic ring;
Q is a group of formula:

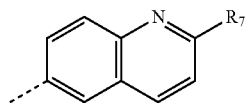

wherein R₇ is a group of the formula:

W²—X²—Y²—X³—Z² wherein
W² is a linker group of the formula —[CR$^x$R$^y$]$_r$— in which r is 1, R$^x$ is hydrogen and R$^y$ is hydrogen or methyl;
X² is absent;
Y² is absent;
X³ is absent; and
Z² is a 4, 5, 6 or 7-membered nitrogen-linked heterocyclyl optionally comprising one further nitrogen atom; and
wherein Z² is optionally further substituted by one or more substituent groups independently selected from oxo, halo, cyano, hydroxy, carboxy, NR$^{dd}$R$^{ee}$, (1-4C)alkyl, (1-4C)alkyl, (3-6C)cycloalkyl, (3-6C)cycloalkyl(1-2C)alkyl, (2C)alkanoyl, (1-2C)alkylsulphonyl, C(O)NR$^{dd}$R$^{ee}$, NR$^{dd}$C(O)R$^{ee}$, NR$^{dd}$SO₂R$^{ee}$ and SO₂NR$^{dd}$R$^{ee}$; wherein R$^{dd}$ and R$^{ee}$ are each independently selected from hydrogen, (1-4C)alkyl, (3-6C)cycloalkyl.

2. A compound according to claim 1, wherein said compound is of formula Ia1, Ia2, Ia3, or Ia4:

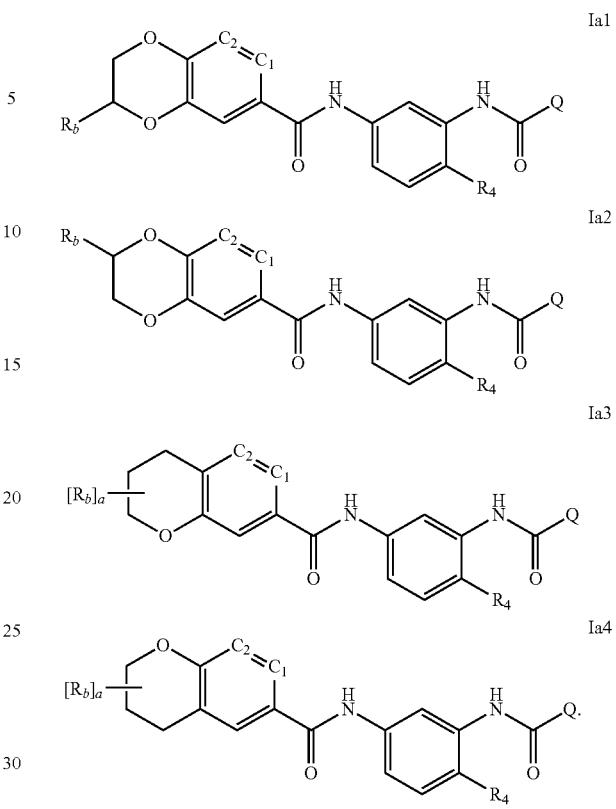

3. A compound according to claim 1, wherein:
C₁ is CR$_{a1}$, wherein R$_{a1}$ is selected from hydrogen, fluoro, chloro, cyano, methyl, methoxy, —CF₃ or —OCF₃;
C₂ is CR$_{a2}$ wherein Rae is selected from hydrogen, fluoro, chloro, cyano, methyl, methoxy, —CF₃ or —OCF₃;
a is 0 or 1; and
R$_b$ is methyl.

4. A compound according to claim 1, wherein R₄ is selected from hydrogen, fluoro, chloro, bromo, iodo, CF₃, OCF₃, cyano, (1-4C)alkyl, (1-4C)alkoxy, or a group of the formula:

W—X—Y—Z wherein
W is absent or (1-3C)alkylene;
X is —O— or —N(R⁴⁰)—, wherein R⁴⁰ is selected from hydrogen or (1-2C)alkyl;
Y is absent or a (1-3C)alkylene;
Z is hydrogen, (1-6C)alkyl, (3-6C)cycloalkyl or a 4 to 10-membered monocyclic or bicyclic heterocyclic ring;
or Y and Z are linked with R⁴⁰ such that, together with the nitrogen atom to which they are attached, they form 4 to 10-membered monocyclic or bicyclic heterocyclic ring optionally comprising one or two further heteroatoms selected from N, O or S;
and wherein any alkylene, alkyl, cycloalkyl or heterocyclyl group present in a R₄ substituent group is optionally further substituted by one or more substituent groups independently selected from halo, hydroxy, cyano, -M-NR⁴¹R⁴², -M-S(O)$_d$R⁴¹, (1-5C)alkyl, (1-5C)alkoxy, (1-5C)haloalkyl or (1-5C)haloalkoxy, and wherein M is absent or (1-4C)alkylene, and R⁴¹ and R⁴² are each independently selected from hydrogen or (1-5C)alkyl.

5. A compound according to claim 1, wherein said compound is selected from formula Ia5, Ia6, Ia7, or Ia8:

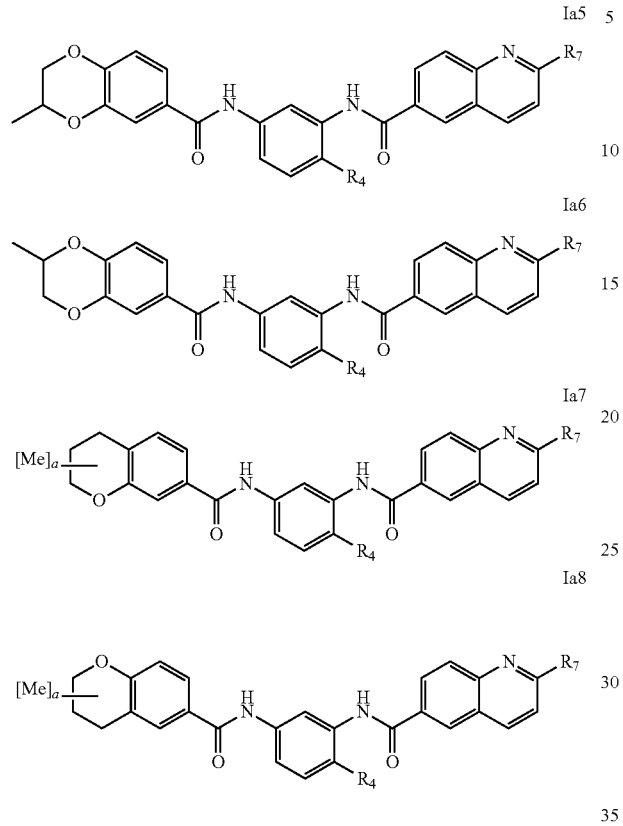

wherein a is 0 or 1.

6. A compound according to claim 5, wherein $R_4$ is methyl or fluoro.

7. A compound according to claim 6, wherein $R_7$ is methyl.

8. A compound according to claim 7, wherein m is 0.

9. A compound according to claim 1, which is selected from any one of the following:

N-(5-(chroman-7-carboxamido)-2-methylphenyl)-2-methylquinoline-6-carboxamide;
N-(5-(chroman-7-carboxamido)-2-fluorophenyl)-2-methylquinoline-6-carboxamide;
N-(5-(chroman-7-carboxamido)-2-fluorophenyl)-2-(4-ethylpiperazin-1-yl)methyl)quinoline-6-carboxamide;
N-(2-chloro-5-(chroman-7-carboxamido)phenyl)-2-methylquinoline-6-carboxamide;
2-(azetidin-1-ylmethyl)-N-(2-chloro-5-(chroman-7-carboxamido)phenyl)quinoline-6-carboxamide;
rac-2-methyl-N-(2-methyl-5-(3-methyl-2,3-dihydrobenzo[b][1,4]dioxine-6-carboxamido)phenyl)quinoline-6-carboxamide;
rac-N-(2-fluoro-5-(3-methyl-2,3-dihydrobenzo[b][1,4]dioxine-6-carboxamido)phenyl)-2-methylquinoline-6-carboxamide;
2-((4-ethylpiperazin-1-yl)methyl)-N-(2-fluoro-5-(3-methyl-2,3-dihydrobenzo[b][1,4]dioxine-6-carboxamido)phenyl)quinoline-6-carboxamide;
N-(2-chloro-5-(3-methyl-2,3-dihydrobenzo[b][1,4]dioxine-6-carboxamido)phenyl)-2-((4-ethylpiperazin-1-yl)methyl)quinoline-6-carboxamide;
2-(azetidin-1-ylmethyl)-N-(2-chloro-5-(3-methyl-2,3-dihydrobenzo[b][1,4]dioxine-6-carboxamido)phenyl)quinoline-6-carboxamide;
2-(azetidin-1-ylmethyl)-N-(2-fluoro-5-(3-methyl-2,3-dihydrobenzo[b][1,4]dioxine-6-carboxamido)phenyl)quinoline-6-carboxamide;
2-methyl-N-(5-(3-methyl-2,3-dihydrobenzo[b][1,4]dioxine-6-carboxamido)-2-(3-(pyrrolidin-1-yl)propyl)phenyl)quinoline-6-carboxamide; and
N-(5-(chroman-7-carboxamido)-2-(3-(pyrrolidin-1-yl)propyl)phenyl)-2-methylquinoline-6-carboxamide;

or a pharmaceutically acceptable salt thereof.

10. A pharmaceutical composition comprising a compound according to claim 1, or a pharmaceutically acceptable salt thereof, in admixture with a pharmaceutically acceptable diluent or carrier.

11. A compound of formula Ib shown below, or a pharmaceutically acceptable salt thereof:

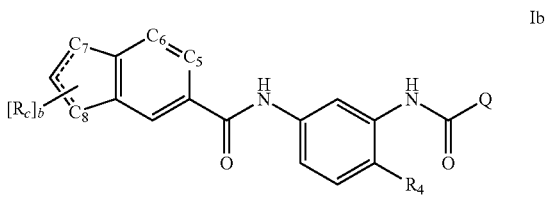

wherein
$C_5$ is $CR_{a5}$;
$C_6$ is $CR_{a6}$;
$R_{a5}$ and $R_{a6}$ are each independently selected from hydrogen, fluoro, chloro, cyano, (1-2C)alkyl, (1-2C)alkoxy or (1-2C)haloalkyl;
$C_7$ is O or CH;
$C_8$ is O or CH;
b is 0, 1 or 2;
$R_c$ is selected from fluoro or (1-2C)alkyl;
subject to the proviso that:
(i) one or both of $C_7$ or $C_8$ is O;
$R_4$ is selected from hydrogen, fluoro, chloro, bromo, iodo, $CF_3$, $OCF_3$, cyano, $NO_2$, (1-4C)alkyl, (1-4C)alkoxy, or a group of the formula:

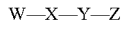

wherein:
W is absent or (1-3C)alkylene;
X is —O— or —N($R^{40}$)—, wherein $R^{40}$ is selected from hydrogen or (1-2C)alkyl;
Y is absent or a (1-3C)alkylene;
Z is hydrogen, (1-6C)alkyl, (3-6C)cycloalkyl or a 4 to 10-membered monocyclic or bicyclic heterocyclic ring;
or Y and Z are linked with $R^{40}$ such that, together with the nitrogen atom to which they are attached, they form 4 to 10-membered monocyclic or bicyclic heterocyclic ring;
and wherein any alkylene, alkyl, cycloalkyl or heterocyclyl group present in a $R_4$ substituent group is optionally further substituted by one or more substituent groups independently selected from oxo, halo, nitro, hydroxy, cyano, carboxy, -M-$NR^{41}R^{42}$, -M-S(O)$_q R^{41}$, -M-C(O)$NR^{41}R^{42}$, -M-$NR^{41}$C(O)$R^{42}$, -M-$NR^{41}$S(O)$_2$ $R^{42}$; -M-S(O)$_2 NR^{41}R^{42}$, (1-5C)alkyl, (1-5C)alkoxy, (1-5C)haloalkyl, (1-5C)haloalkoxy or (1-5C)alkanoyl, and wherein M is absent or (1-4C)alkylene, and $R^{41}$ and $R^{42}$ are each independently selected from hydrogen or (1-5C)alkyl; or $R^{41}$ and $R^{42}$ can be linked such that, together with the nitrogen atom to which they are attached, they form a 4-6-membered heterocyclic ring;

Q is a group of formula:

[structure: quinoline with R7 substituent at 2-position, attachment at 6-position]

wherein R₇ is a group of the formula:

W²—X²—Y²—X³—Z² wherein

W² is a linker group of the formula —[CR$^x$R$^y$]$_r$— in which r is 1, R$^x$ is hydrogen and R$^y$ is selected from hydrogen or methyl;

X² is absent;

Y² is absent;

X³ is absent; and

Z² is a 4, 5, 6 or 7-membered nitrogen-linked heterocyclyl optionally comprising one further nitrogen atom;

and wherein Z² is optionally further substituted by one or more substituent groups independently selected from oxo, halo, cyano, hydroxy, carboxy, NR$^{dd}$R$^{ee}$, (1-4C)alkoxy, (1-4C)alkyl, (3-6C)cycloalkyl, (3-6C)cycloalkyl(1-2C)alkyl, (2C)alkanoyl, (1-2C)alkylsulphonyl, C(O)NR$^{dd}$R$^{ee}$, NR$^{dd}$C(O)R$^{ee}$, NR$^{dd}$SO$_2$R$^{ee}$ and SO$_2$NR$^{dd}$R$^{ee}$; wherein R$^{dd}$ and R$^{ee}$ are each independently selected from hydrogen, (1-4C)alkyl, (3-6C)cycloalkyl.

12. A compound according to claim 11, wherein said compound is of formula Ib1, or Ib2:

Ib1

[structure]

Ib2

[structure]

13. A compound according to claim 11, wherein said compound is of formula Ib3, Ib4, Ib5 or Ib6:

Ib3

[structure]

Ib4

[structure]

Ib5

[structure]

Ib6

[structure]

wherein each b is independently 0 or 1.

14. A compound according to claim 11, wherein R₄ is selected from hydrogen, fluoro, chloro, bromo, iodo, CF₃, OCF₃, cyano, (1-4C)alkyl, (1-4C)alkoxy, or a group of the formula:

W—X—Y—Z wherein

W is absent or (1-3C)alkylene;

X is —O— or —N(R⁴⁰)—, wherein R⁴⁰ is hydrogen or (1-2C)alkyl;

Y is absent or a (1-3C)alkylene;

Z is hydrogen, (1-6C)alkyl, (3-6C)cycloalkyl or a 4 to 10-membered monocyclic or bicyclic heterocyclic ring;

or Y and Z are linked with R⁴⁰ such that, together with the nitrogen atom to which they are attached, they form a 4 to 10-membered monocyclic or bicyclic heterocyclic ring optionally comprising one or two further heteroatoms selected from N, O or S;

and wherein any alkylene, alkyl, cycloalkyl or heterocyclyl group present in a R₄ substituent group is optionally further substituted by one or more substituent groups independently selected from halo, hydroxy, cyano, -M-NR⁴¹R⁴², -M-S(O)$_q$R⁴¹, (1-5C)alkyl, (1-5C)alkoxy, (1-5C)haloalkyl or (1-5C)haloalkoxy, and wherein M is absent or (1-4C)alkylene, and R⁴¹ and R⁴² are each independently hydrogen or (1-5C)alkyl.

15. A compound according to claim 13, wherein R₄ is methyl or fluoro.

16. A compound according to claim 15, wherein R₇ is methyl.

17. A compound according to claim 11 which is selected from any one of the following:

N-(5-(2,3-dihydrobenzofuran-6-carboxamido)-2-methylphenyl)-2-methylquinoline-6-carboxamide;

N-(5-(2,3-dihydrobenzofuran-5-carboxamido)-2-methylphenyl)-2-methylquinoline-6-carboxamide;

N-(5-(2,3-dihydrobenzofuran-6-carboxamido)-2-fluorophenyl)-2-((4-ethylpiperazin-1-yl)methyl)quinoline-6-carboxamide;

N-(5-(benzofuran-6-carboxamido)-2-methylphenyl)-2-methylquinoline-6-carboxamide;

N-(2-chloro-5-(2,3-dihydrobenzofuran-6-carboxamido)phenyl)-2-((4-ethylpiperazin-1-yl)methyl)quinoline-6-carboxamide;

N-(5-(2,3-dihydrobenzofuran-6-carboxamido)-2-methylphenyl)-2-((4-ethylpiperazin-1-yl)methyl)quinoline-6-carboxamide;

N-(5-(2,3-dihydrobenzofuran-6-carboxamido)-2-fluorophenyl)-2-methylquinoline-6-carboxamide;

N-(2-chloro-5-(2,3-dihydrobenzofuran-6-carboxamido)phenyl)-2-methylquinoline-6-carboxamide;

rac-2-methyl-N-(2-methyl-5-(2-methyl-2,3-dihydrobenzofuran-5-carboxamido)phenyl)quinoline-6-carboxamide;

2-(azetidin-1-ylmethyl)-N-(2-chloro-5-(2,3-dihydrobenzofuran-6-carboxamido)phenyl)quinoline-6-carboxamide;

2-(azetidin-1-ylmethyl)-N-(5-(2,3-dihydrobenzofuran-6-carboxamido)-2-fluorophenyl)quinoline-6-carboxamide;

(rac)-2-methyl-N-(2-methyl-5-(2-methyl-2,3-dihydrobenzofuran-6-carboxamido)phenyl)quinoline-6-carboxamide;

N-(5-(benzo[d][1,3]dioxole-5-carboxamido)-2-methylphenyl)-2-methylquinoline-6-carboxamide;

N-(5-(2,3-dihydrobenzofuran-6-carboxamido)-2-(3-(pyrrolidin-1-yl)propyl)phenyl)-2-methylquinoline-6-carboxamide; and 2-methyl-N-(5-(2-methyl-2,3-dihydrobenzofuran-6-carboxamido)-2-(3-(pyrrolidin-1-yl)propyl)phenyl)quinoline-6-carboxamide;

or a pharmaceutically acceptable salt thereof.

18. A pharmaceutical composition comprising a compound according to claim 11, or a pharmaceutically acceptable salt thereof, in admixture with a pharmaceutically acceptable diluent or carrier.

* * * * *

UNITED STATES PATENT AND TRADEMARK OFFICE
CERTIFICATE OF CORRECTION

Page 1 of 1

PATENT NO. : 10,647,678 B2
APPLICATION NO. : 15/563501
DATED : May 12, 2020
INVENTOR(S) : Keith Jones et al.

It is certified that error appears in the above-identified patent and that said Letters Patent is hereby corrected as shown below:

In the Claims

In Claim 3, Column 72, Line 37, cancel the text:
"wherein Rae is selected from"
And insert:
-- wherein $R_{a2}$ is selected from --

In Claim 9, Column 73, Line 48, cancel the text:
"N-(5-(chroman-7-carboxamido)-2-fluorophenyl)-2-(4-"
And insert:
-- N-(5-(chroman-7-carboxamido)-2-fluorophenyl)-2-((4- --

In Claim 9, Column 73, Line 64, cancel the text:
"methyl)quinoline-6-carboxamide"
And insert:
-- methyl)quinoline-6-carboxamide; --

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*